(12) United States Patent
Lacirignola et al.

(10) Patent No.: US 10,264,999 B2
(45) Date of Patent: Apr. 23, 2019

(54) HIGH FIDELITY SYSTEMS, APPARATUS, AND METHODS FOR COLLECTING NOISE EXPOSURE DATA

(71) Applicant: Massachusetts Institute of Technology, Cambridge, MA (US)

(72) Inventors: Joseph J. Lacirignola, Beverly, MA (US); Trina Rae Vian, Westford, MA (US); Christopher J. Smalt, Arlington, MA (US); David F. Aubin, Jr., Pelham, NH (US); David C. Maurer, Stoneham, MA (US); Mary Katherine Byrd, Arlington, MA (US); Christine M. Weston, Cambridge, MA (US); Kerry A. Johnson, Somerville, MA (US); Shakti Davis, Arlington, MA (US); Olha Townsend, Providence, RI (US); Paul T. Calamia, Framingham, MA (US); Edward H. Chen, Woodland Hills, CA (US); Paula P. Collins, Arlington, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 15/863,027

(22) Filed: Jan. 5, 2018

(65) Prior Publication Data

US 2018/0140233 A1    May 24, 2018

Related U.S. Application Data

(63) Continuation of application No. PCT/US2017/049919, filed on Sep. 1, 2017.
(Continued)

(51) Int. Cl.
*G01H 3/14* (2006.01)
*G01H 3/12* (2006.01)
(Continued)

(52) U.S. Cl.
CPC ............ *A61B 5/125* (2013.01); *A61B 5/6814* (2013.01); *A61B 5/721* (2013.01); *G01H 3/12* (2013.01); *G01H 3/14* (2013.01)

(58) Field of Classification Search
CPC ..... G10K 11/178; A61B 5/125; A61B 5/6814; A61B 5/721; G01H 3/12
(Continued)

(56) References Cited

U.S. PATENT DOCUMENTS

| 3,802,535 A | 4/1974 | Peake et al. |
| 4,985,925 A | 1/1991 | Langberg et al. |

(Continued)

FOREIGN PATENT DOCUMENTS

| CA | 2293522 A1 | 10/2000 |
| CN | 101690256 A | 3/2010 |

(Continued)

OTHER PUBLICATIONS

International Search Report and Written Opinion dated May 1, 2018 for International Application No. PCT/US2017/049919, 14 pages.
(Continued)

*Primary Examiner* — J M Saint Surin
(74) *Attorney, Agent, or Firm* — Smith Baluch LLP

(57) ABSTRACT

Systems, apparatus, and methods for collecting, interpreting, and utilizing noise exposure data may include sensors to obtain an analog signal representative of impulse noise sound pressure and an analog signal representative of continuous noise sound pressure. At least one ADC may generate digital signals by sampling the analog signals at rates equal to or greater than twice the reciprocal of a minimum
(Continued)

impulse noise rise time. Accelerometers may obtain data in close proximity to and remote from the sensors. At least one processor may include a first combining node to combine the digital signals to represent both the continuous noise and the impulse noise, a shock-artifact detection filter to identify a time frame including a shock artifact based on the accelerometry data, a frequency filter to generate a background-removed audio signal, an adaptive filter to estimate the shock artifact, and a second combining node to produce a shock-artifact-free audio signal.

15 Claims, 27 Drawing Sheets

Related U.S. Application Data

(60) Provisional application No. 62/384,409, filed on Sep. 7, 2016.

(51) Int. Cl.
 *A61B 5/00* (2006.01)
 *A61B 5/12* (2006.01)

(58) Field of Classification Search
 USPC .......................................................... 73/646
 See application file for complete search history.

(56) References Cited

U.S. PATENT DOCUMENTS

| | | | |
|---|---|---|---|
| H1726 H | 5/1998 | Chen | |
| 5,757,930 A | 5/1998 | Seidmann et al. | |
| 5,970,795 A | 10/1999 | Seidmann et al. | |
| 7,401,519 B2* | 7/2008 | Kardous | G01H 3/06 |
| | | | 381/56 |
| 7,836,770 B2 | 11/2010 | Goldberg et al. | |
| 7,882,743 B2 | 2/2011 | Goldberg et al. | |
| 9,478,229 B2 | 10/2016 | Lacirignola et al. | |
| 10,074,397 B2 | 9/2018 | Lacirignola et al. | |
| 2004/0179697 A1 | 9/2004 | Griesinger | |
| 2006/0219015 A1 | 10/2006 | Kardous | |
| 2007/0058031 A1 | 3/2007 | Aizawa | |
| 2007/0180915 A1 | 8/2007 | Goldberg et al. | |
| 2007/0186656 A1 | 8/2007 | Goldberg et al. | |
| 2007/0234889 A1* | 10/2007 | Rotolo de Moraes | |
| | | | G10H 1/361 |
| | | | 84/730 |
| 2009/0316916 A1 | 12/2009 | Haila et al. | |
| 2010/0119077 A1 | 5/2010 | Platz et al. | |
| 2010/0278350 A1 | 11/2010 | Rung | |
| 2011/0170117 A1 | 7/2011 | Fischer | |
| 2013/0197725 A1* | 8/2013 | O'Dell | H04L 67/125 |
| | | | 701/14 |
| 2015/0162047 A1 | 6/2015 | Lacirignola et al. | |
| 2016/0320231 A1 | 11/2016 | Mirov et al. | |
| 2017/0019741 A1 | 1/2017 | Lacirignola et al. | |
| 2018/0132779 A1* | 5/2018 | VanDam | A61B 5/4803 |
| 2018/0288542 A1 | 10/2018 | Lacirignola et al. | |

FOREIGN PATENT DOCUMENTS

| | | |
|---|---|---|
| CN | 102150439 A | 8/2011 |
| EP | 2177043 A1 | 4/2010 |
| EP | 2338287 A1 | 6/2011 |
| EP | 2177043 B1 | 6/2012 |
| EP | 2501153 A1 | 9/2012 |
| GB | 2349466 A1 | 11/2000 |
| GB | 2349466 B | 10/2003 |
| JP | 7308847 A | 11/1995 |
| JP | 2008212127 A | 9/2008 |
| JP | 2008297001 A | 12/2008 |
| JP | 2012502576 W | 1/2012 |
| JP | 4936252 B2 | 5/2012 |
| JP | 4960769 B2 | 6/2012 |
| KR | 2011059639 A | 6/2011 |
| SU | 580900 | 12/1977 |
| WO | WO 2009006897 A1 | 1/2009 |
| WO | WO 2010029509 A1 | 3/2010 |

OTHER PUBLICATIONS

"Advanced Personal Noise Monitoring", 3M Occupational Health & Environment Safety Division NoisePro Brochure (2013), 4 pages.
"Etymotic takes the cost and complication our of noise dosimetry", Etymotic Research Inc., Information Sheet ER078105-C (2010), 2 pages.
"Noise Sentry", Data Sheet (2009), 5 pages.
"Personal Sound Exposure Meter," Casella CEL Brochure (2011), 8 pages.
"Preventing Occupational Hearing Loss—A Practical Guide", National Institute for Occupational Safety and Health, Publication No. 96-110 (1996), 5 pages.
"Super-duty Noise Dosimeters", Spark Family of Noise Dosimeters, Larson Davis A PCB Piezotronics Div., Information Sheet (2009), 4 pages.
Ahroon et al., "Analysis of Army-wide hearing conservation database for hearing proles related to crew-served and individual weapon systems," Noise & Health 13, pp. 76-83 (2011).
American Institute of Biological Sciences (AIBS), Peer Review of Impulse Noise Injury Models, Nov. 9, 2010), 15 pages.
American National Standards Institute (ANSI), Specification for Sound Level Meters, S1.4-1983 (R2006) (ANSI 1983), 32 pages.
ANSI, Specification for Personal Noise Dosimeters, S1.25-1991 (ASA 98-1991) (ANSI 1991), 20 pages.
Basch, "A wearable pocket noise dosimeter", Conference Date: Apr. 18-27, *Program of the 83rd meeting of the Acoustical Society of America*, 180, vol. 52, No. 1 (Part 1) (1972), 1 page.
Boroditsky et al., "Predicting shipboard noise using 3-d acoustic modeling," Noise Control Eng. J. 55, 246-56 (2007).
Bruel, "Do we measure damaging noise correctly?" Noise Control Eng. J. 8, 52-60 (1997).
Cooper et al., "The Department of Defense epidemiologic and economic burden of hearing loss study," Military Med. 179, 1458-64 (2014).
Defence Res. & Dev. Canada, Toronto Research Centre, DRDC-RDDC-2015-R243, "A comparison of metrics for impulse noise exposure," (2015), 52 pages.
Fowler, "Instrumentation for noise and vibration measurement (excerpts from Chapter 6, Handbook of Noise Measurement)", Conference Date: May 13-17, Proceedings of the Short Courses, Fundamentals of Noise Control and Reduction of Machinery Noise, pp. 124-139 (1974).
Goley et al., "Kurtosis-corrected sound pressure level as a noise metric for risk assessment of occupational noises," J. Acoustical Society of America 129, 1475-81 (2011).
Hamernik et al., "Interaction of continuous and impulse noise: Audiometric and histological effects," J. Acoustical Society of America 55, 117-21 (1974).
Hamernik et al., "The energy spectrum of an impulse: Its relation to hearing loss," J. Acoustical Society of America 90, 197-204 (1991).
Helfer et al, "Noise-induced hearing injury and comorbidities among postdeployment US Army soldiers: Apr. 2003-Jun. 2009," Am. J. Audiology 20, 33-41 (2011).
Henderson et al., "Impulse noise: critical review", Acoustical Society of America, vol. 80, No. 2, pp. 569-584 (1986).
Johnson, "New Auditory Damage Risk Criteria and Standard for Impulse Noise", RTO HFM Lecture Series, pp. 2-9 (2000).
Kardous et al., "Evaluation of smartphone sound measurement applications," J. Acoustical Society of America, 135, EL186-EL192 (2014), 8 pages.
Kardous et al., "Limitations of using dosimeters in impulse noise environments," J. Occup. & Envt'l Hygiene 1, 456-62 (2004).
Kardous et al., "Noise dosimeter for monitoring exposure to impulse noise," Applied Acoustics 66, 974-85 (2005).

(56) References Cited

OTHER PUBLICATIONS

Stevin, "Integrating sound level meter for the measurement of continuous and impulse noise", Revue d'Acoustique, vol. 13, No. 55, pp. 241-244 (1980).
Kenna, "Impulse Noise Measurement Systems." Proceedings—1981 International Conference on Noise Control Engineering, Internoise 81: Practice of Noise Control Engineering, pp. 985-988 (1981).
Knowles Electronics, Inc., Walk induced head vibrations and hearing aid design TB5; 1-4 (1961).
Kryter, "The Effects of Noise on Man," (Academic 1985); 96 pages.
Kuhn, "The pressure transformation from a diffuse sound field to the external ear and to the body and head surface," J. Acoustical Society of America 65, 991-1000 (1979).
Le Prell et al., "Prevention of Noise-Induced Hearing Loss: Potential Therapeutic Agents," in Springer Handbook of Auditory Res., 40:285-338 (Springer 2012).
Li, "A brief review: acoustic emission method for tool monitoring during turning", International Journal of Machine Tools & Manufacture 42, pp. 157-165 (2002).
McKinley, "LIAeq100ms, an a-duration adjusted impulsive noise damage risk criterion," J. Acoustical Society of America 138:1774; http://asa.scitation.org/doi/10.1121/1.4933614. Abstract, 3 pages.
Nakashima et al., "Hearing, communication and cognition in low-frequency noise from armoured vehicles," Noise & Health 9:35-41 (2007).
Nakashima et al., "Review of weapon noise measurement and damage risk criteria: Considerations for auditory protection and performance," Military Med. 180:402-408 (2015).
Notification of Transmittal of the International Search Report and the Written Opinion of the International Searching Authority in International Application No. PCT/US2014/69116, filed Dec. 8, 2014, dated Aug. 13, 2015, 9 pages.
Passchier-Vermeer et al., "Measurement of impulse noise at workplaces: relation between oscilloscopic measurements with an ordinary precision sound level meter", Conference Date: Aug. 25-27, 1980, Scandinavian Audiology Supplementum, No. 12, pp. 85-97 (1980).
Price et al., "Insights into hazard from intense impulses from a mathematical model of the ear," J. Acoustical Society of America 90:219-27 (1991).
Price, "Assumptions in the measurement of impulse noise", Sound and Vibration, vol. 15, No. 10, pp. 8-9 (1981).
Price, "Implications of a critical level in the ear for assessment of noise hazard at high intensities", Journal of Acoustical Society of America, vol. 69, pp. 171-177, (1981).
Price, "Impulse noise hazard as a function of level and spectral distribution," in Salvi et al., Basic and Applied Aspects of Noise-Induced Hearing Loss, pp. 379-392 (Springer 1986).
Price, "Validation of the Auditory Hazard Assessment Algorithm for the Human with impulse noise data," J. Acoustical Society of America 122:2786-2802 (2007).
Qiu et al., "The kurtosis metric as an adjunct to energy in the prediction of trauma from continuous, non-Gaussian noise exposures," J. Acoustical Society of America 120:3901-06 (2006).
Qiu et al., "The value of a kurtosis metric in estimating the hazard to hearing of complex industrial noise exposures," J. Acoustical Society of America, 133:2856-66 (2013).
Rovig et al., "Hearing health risk in a population of aircraft carrier flight deck personnel," Military Med. 169:429-32 (2004).
Shaw et al., "Transformation of sound-pressure level from the free field to the eardrum presented in numerical form," J. Acoustical Society of America 78:1120-23 (1985).
Sheeld et al., "The relationship between hearing acuity and operational performance in dismounted combat," in Proceedings of the Human Factors and Ergonomics Society Annual Meeting 59:1346-50 (2015).
Singh, "Wearable Noise Dosimeter", Noise Control Vibration Reduction, 4/6, pp. 250-254 (1973).
Sun et al., "Development and validation of a new adaptive weighting for auditory risk assessment of complex noise," Applied Acoustics 103:30-36 (2016).
Theodoroff et al., "Hearing impairment and tinnitus: Prevalence, risk factors, and outcomes in US service members and veterans deployed to the Iraq and Afghanistan wars," Epidem. Rev., 37:71-85 (2015).
U.S. Army Med. Res. & Dev. Command, Blast overpressure studies with animals and man: Walk-up study (1993), 71 pages.
U.S. Army Res. Lab., ARL-RP-0521, Mathematical Model of the Ear's Response to Weapons Impulses (2015), 26 pages.
U.S. Department of Veterans Affairs, Annual Benefits Report Fiscal Year 2015 (2015), 224 pages.
U.S. Dept. of Defense, 6055.12, Hearing Conservation Program (2010), 26 pages.
U.S. Dept. of Health & Human Services, 98-126, Criteria for a Recommended Standard: Occupational Noise Exposure (1998).
U.S. Dept. of Health & Human Services, EPHB 309-05h, An Analysis of the Blast Overpressure Study Data Comparing Three Exposure Criteria (2009), 61 pages.
U.S. Dept. of Interior, Bureau of Mines, Response Variations of a Microphone Worn on the Human Body 53 pages. (1973).
U.S. Navy, 5100.19E, Safety and Occupational Health (SOH) Program Manual for Force Afloat ch. B4 (2007), 230 pages.
Von Gierke et al., "Daily Noise Exposure of Populations," 10th International Congress on Acoustics. vol. 3: Contributed Papers Continued (1980), 2 pages.
Ward et al., "Effective quiet and moderate TTS: Implications for noise exposure standards," J. Acoustical Society of America, 59:160-65 (1976).
Xiangfeng, "Application of sound analysis technique to monitor tool wear during the turning process", ICPMT2006—Progress of Machining Technology—Proceedings of the 8th International Conference on Progress of Machining Technology (2006), 1 page.
Yankaskas et al., "Landing on the roof: CVN noise," Naval Eng. J., 111:23-34 (1999).
Zagadou et al., "Impulse noise injury prediction based on the cochlear energy," Hearing Research 1-16 (2016).
U.S. Department of Defense, Design Criteria Standard Noise Limits. Released Apr. 15, 2015. 123 pages.

* cited by examiner

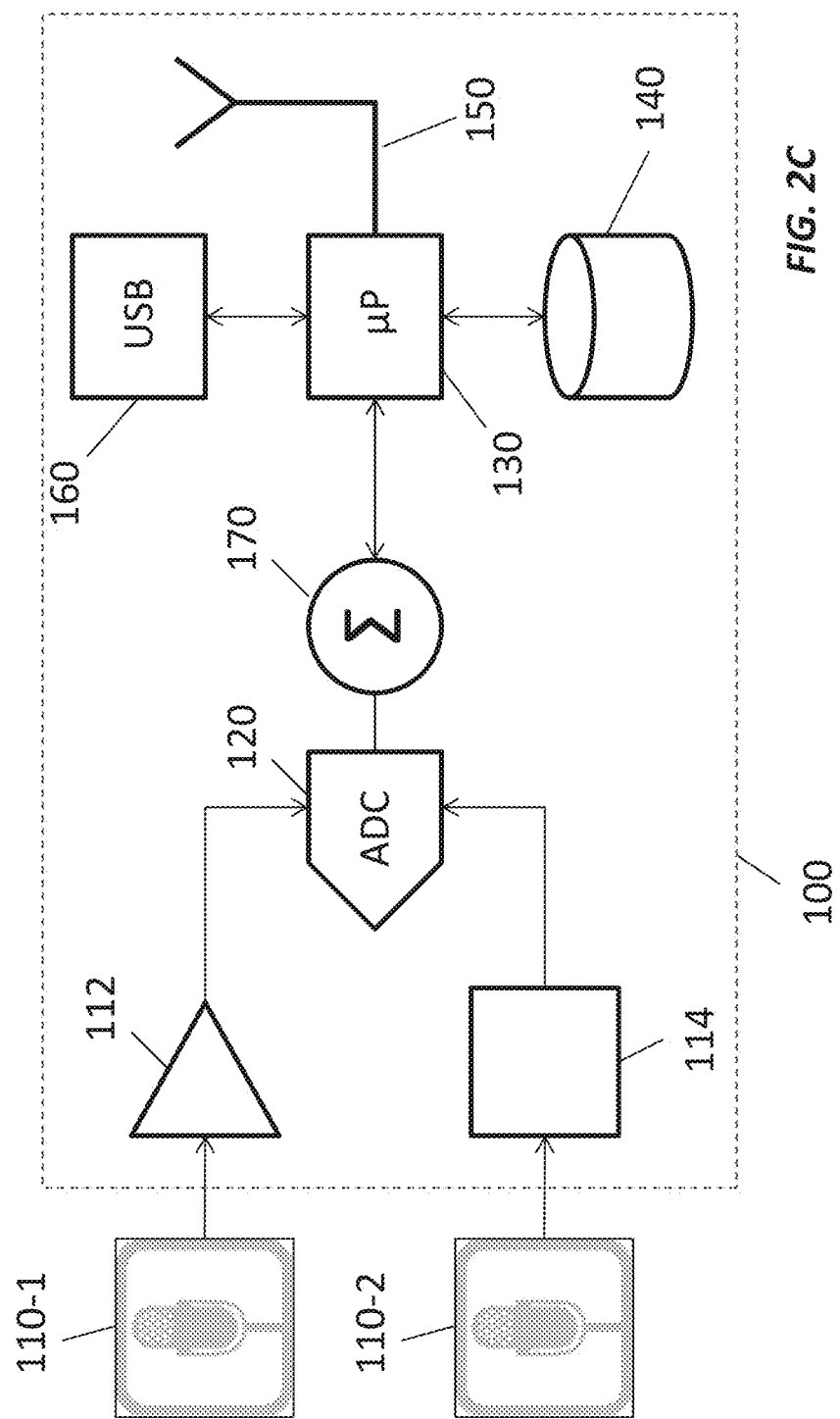

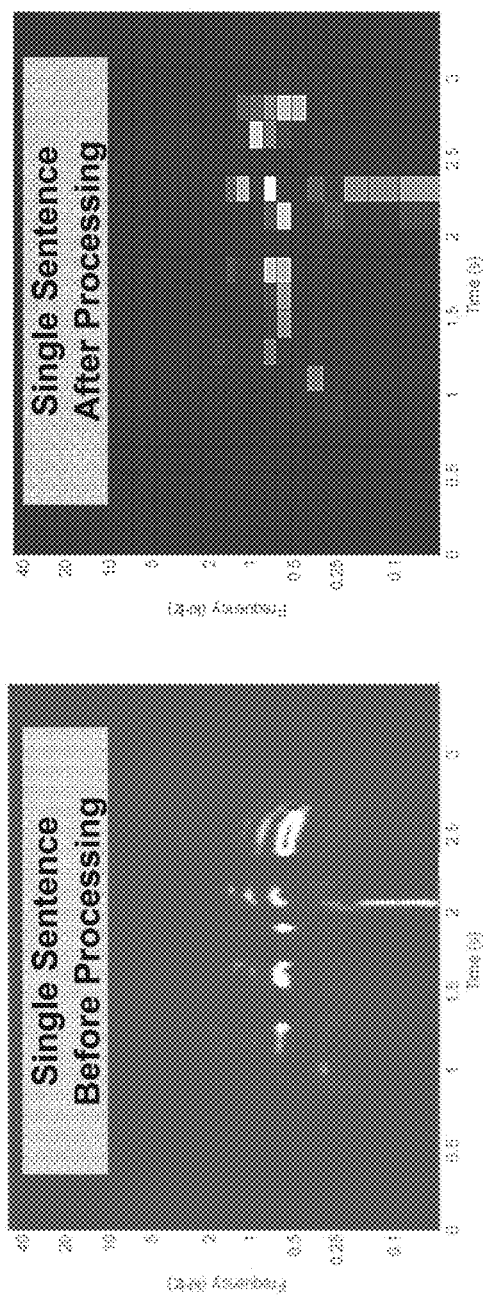

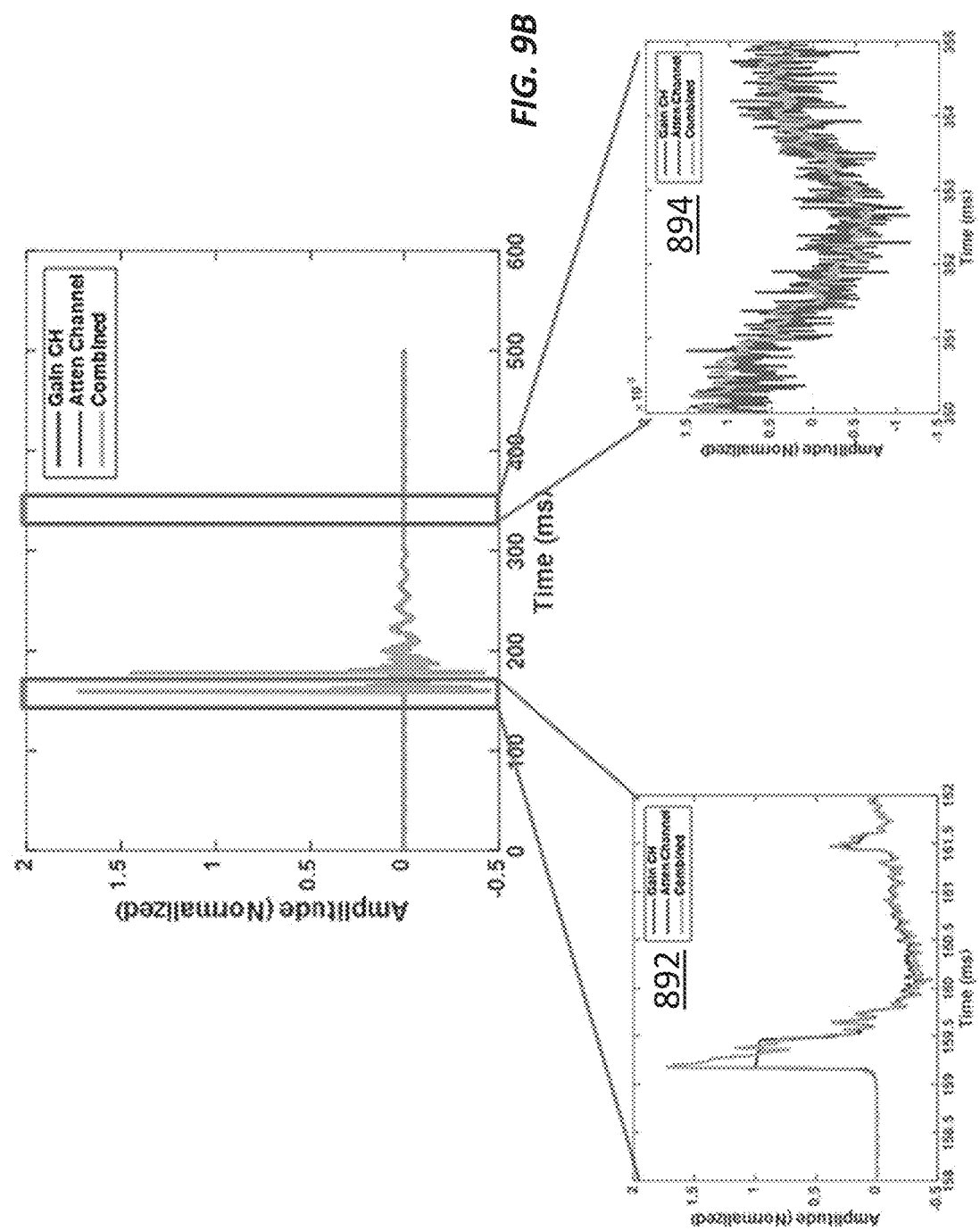

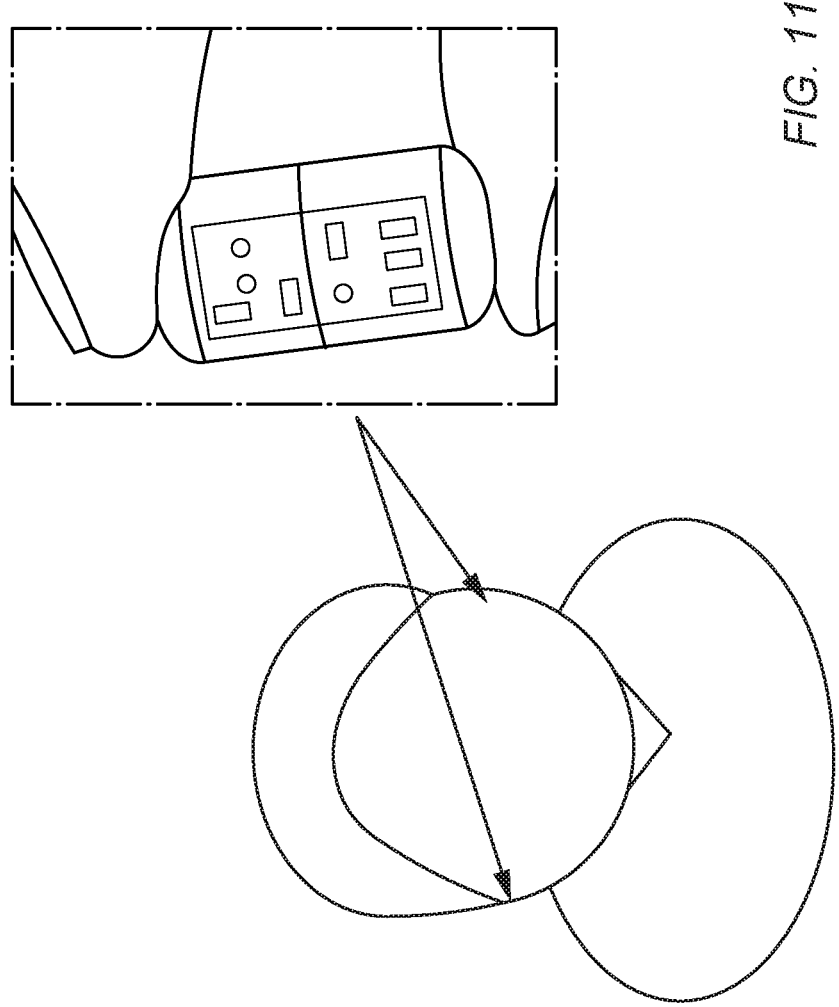

HIGH FIDELITY SYSTEMS, APPARATUS, AND METHODS FOR COLLECTING NOISE EXPOSURE DATA

CROSS-REFERENCE TO RELATED APPLICATIONS

This application is a bypass continuation of International Application PCT/US2017/049919, entitled "High Fidelity Systems, Apparatus, and Methods for Collecting Noise Exposure Data" and filed Sep. 1, 2017, which in turn claims priority, under 35 U.S.C. § 119, to U.S. Application No. 62/384,409, entitled "High Fidelity Systems, Apparatus, and Methods for Collecting Noise Exposure Data" and filed Sep. 7, 2016. Each of these applications is incorporated herein by reference in its entirety.

GOVERNMENT SUPPORT

This invention was made with government support under Contract No. FA8721-05-C-0002 awarded by the United States Air Force. The government has certain rights in the invention.

TECHNICAL FIELD

The present disclosure relates generally to systems, apparatus, and methods for collecting, interpreting, and utilizing noise exposure data. More specifically, the present disclosure relates to systems, apparatus, and methods for recording time-varying acoustic pressure, both continuous noise and impulse noise.

BACKGROUND

Noise generally is classified as continuous (exhibiting only small changes in level over time), intermittent (interrupted by occasional increases in level), impulsive (containing components with sharp rises and rapid decays), or complex (a combination of the above), and the frequency range and level can vary with the type and source of the noise.

Noise-induced hearing loss (NIHL) is hearing loss caused by loud sounds. NIHL can be caused by a single exposure to an intense "impulse" sound, such as an explosion, or by repeated or continuous exposure to loud sounds over an extended period of time, such as noise generated in a woodworking shop. NIHL is not understood completely, but current models of NIHL suggest that sounds at levels above about 85 dB are likely to damage sensitive structures in the inner ear, leading to hearing loss. Current models of NIHL also suggest that extremely loud impulsive sounds (sounds with rise times shorter than about one second and peak amplitudes over about 85 dB) cause damage more quickly than softer sounds with longer rise times. Loud, impulsive sounds may also cause tinnitus, a condition in which the afflicted person perceives ringing in the ears even under silent conditions.

NIHL affects up to 15% of Americans between the ages of 20 and 69, or about 26 million people total. More than 30,000 cases of noise-induced hearing injuries were reported among active-duty soldiers, sailors, airmen, and Marines in 2010. The number of new tinnitus incidents per year increased 42% from 2007-2010 among service members. In 2009 alone, the government made more than 100,000 new service-connected disability awards for tinnitus and hearing loss. About 10% of veterans' disability payments made for tinnitus and hearing loss; in 2013, hearing loss and tinnitus disability payments totaled about $850,000,000 per year.

Dosimetry involves measuring sound pressure levels (SPLs) in a noise environment with the goal of estimating the total dosage to which an individual is exposed over a period of time. Often the dose is estimated in terms of A-weighted energy in conjunction with the equal-energy hypothesis (EEH), which assumes that accumulated noise energy is sufficient to determine risk of NIHL and that the underlying temporal characteristics of the noise are irrelevant. Under the EEH, two exposures are equivalent if the respective average noise levels and durations comply with a specified exchange rate. For example, a 3-dB exchange rate often is employed such that a halving or doubling of the exposure time is accommodated with a +3 or −3 dB adjustment, respectively, to the allowable noise level.

In an effort to conserve hearing in industrial and military settings, guidelines on the maximum allowable daily noise exposure are recommended by regulating agencies such as National Institute for Occupational Safety and Health (NIOSH) and military branches under the U.S. Department of Defense (DoD) Hearing Conservation Program. This allowable daily noise dosage is expressed as a percent relative to the recommended limit, i.e., 100% dose represents maximum allowable noise exposure for an individual. For exposure in a continuous noise environment, the current military standard design criteria MIL-STD-1474E (2015) sets a limit of 85 dBA for a duration of 8 hours, where the exposure duration and level may be traded off to satisfy an equal-energy criterion using a 3 dB exchange rate.

SUMMARY

Noise dosimeters may be used to measure noise exposure and report the dosage accumulated over the course of a day, work shift or event of interest. The challenges of accurate noise dosimetry are due to a number of factors, including the variety of noise types and environments encountered, and the demands this variety places on dosimeters and their use. Typical commercial noise dosimeters record only peak noise levels and average noise levels over a given sampling period (usually a minute) and fail to retain any spectral information about the recorded sounds.

Typical commercial noise dosimeters are required to operate only up to 140 dB sound-pressure level (SPL) and cover a frequency range similar to that of human hearing. However, weapons fire, blasts, and other impact noises can exceed this SPL limit, and impulses can exhibit acoustic bandwidths extending well beyond the audio spectrum due to their short durations. Thus, dosimeter design, for example with respect to microphone and analog-to-digital converter performance, is critical for measurement success. Dosimeter placement also can affect measured results, as free-field, on-body, and in/near-ear microphone positions can yield variations in measured spectra and levels due to absorption by clothing, head shadowing, and pinna resonances.

Unfortunately, little is known about exposure to impulsive sounds, much less the noise-induced injury mechanisms associated with impulsive sounds. To address this dearth of information about injuries caused by impulsive sounds, the inventors have developed technology to provide audio recordings with broader bandwidths and larger peak amplitudes than conventional noise dosimeters. A high sampling rate, broad spectrum noise dosimeter can record sample rates up to 200 kHz (stereo) to capture fast rise times of impulse noise, over a broad measurement range of SPL (e.g., about 50 dB SPL to about 185 dB SPL). However, until now, no system has existed to measure full spectrum high sampling rate noise histories with a small, lightweight, and lower power device. While fixed dosimetry "stations" may be practical to set up and maintain, spatially-varying noise fields and moving subjects may require individually-worn dosimeters to assess personal noise exposure accurately. Particular strengths of some embodiments include a small form factor, high sampling rate, and simplicity. Thus, some embodiments expand the capabilities of existing noise recorders and dosimeters and enable measurements in contexts and environments in which other devices would likely be impaired or broken.

More specifically, some embodiments include a compact, portable package suitable for acquiring data continuously in particularly rugged environments, such as battlefields, for several hours at a time. The data collected by some embodiments may be used to more precisely estimate the sound exposure experienced by the user and to create more precise models for predicting NIHL. This data also may be used to develop more advanced mitigation techniques, including active hearing protection.

Embodiments of the present invention may include a portable system and corresponding methods for recording sound in an environment subject to impulse noise characterized by an initial rise time, which may be about 50 μs or less. Some examples of the portable system comprise a first microphone, a second microphone, a combining/summing node coupled to the first and second microphones, an analog-to-digital converter (ADC) coupled to the combining/summing node, and a processor coupled to the ADC. In operation, the first microphone, which may be worn on an article of clothing, a hat, a helmet, or a bag, produces a first analog signal representative of sound in a first amplitude range, and the second microphone produces a second analog signal representative of sound in a second amplitude range different than the first amplitude range (e.g., higher or lower than the first amplitude range). The combining/summing node combines the first analog signal and the second analog signal into a combined analog signal with a combined amplitude range that is about equal to the sum of the first amplitude range and the second amplitude range. The ADC samples the combined analog signal at a sampling rate (e.g., about 20 kHz to about 200 kHz) that is equal to or greater than twice the reciprocal of the initial rise time so as to produce a digital signal representative of the combined analog signal. And the processor stores a representation of the digital signal in a nonvolatile memory.

In some cases, the first amplitude range extends from about 115 dB to about 180 dB, the second amplitude range extends from about 75 dB to about 140 dB, and the combined amplitude range extends from about 75 dB to about 180 dB. The portable system may also include an attenuator that is operably coupled to an output of the first microphone and a first input of the combining/summing node in order to attenuate the first analog signal, and an amplifier that is operably coupled to an output of the second microphone and a second input of the combining/summing node in order to amplify the second analog signal.

In certain examples, the processor is configured to identify at least one portion of the digital signal corresponding to at least a portion of the impulse noise. The processor may also (i) divide the digital signal into a plurality of time-frequency bins, (ii) estimate an amount of energy in each time-frequency bin in the plurality of time-frequency bins to produce a plurality of energy estimates, and (iii) store the plurality of energy estimates in the nonvolatile memory as at least a portion of the representation of the digital signal.

Such a processor may also select the distribution and/or sizes of the time-frequency bins so as to non-invertibly blur speech content information in the representation of the digital signal. It may also select the distribution and/or sizes of the time-frequency bins so as to substantially preserve spectral and intensity information of the combined analog signal in the representation of the digital signal.

The portable system may also include a first buffer that is operably coupled to the ADC. In operation, the first buffer stores at least one first sample of the analog signal generated by the ADC. In these examples, the processor may transfer the first sample from the first buffer to the nonvolatile memory and interrupt the transfer to store at least one second sample of the analog signal generated by the ADC in a second buffer operably coupled to the ADC. The processor may also interrupt the transfer based on acquisition of the second sample by the ADC or a signal from a timer.

The portable system may also include a power supply, which is coupled to ADC and the processor, to supply electrical power to the ADC and the processor. In some examples, the portable system also includes a housing disposed at least partially about the combining/summing node, the ADC, the processor, and/or the power supply. It may also include a communications interface, operably coupled to the processor, to transmit the representation of the digital signal to an electronic device.

Other embodiments of the present invention include a portable system for digitizing and recording an analog signal representative of at least one measurement of an environment. This portable system may include an ADC, a first buffer, and a processor. In operation, the ADC generates at least one first sample of the analog signal at a sample rate of about 20 kHz to about 200 kHz. The first buffer, which is operably coupled to the ADC, stores at least one first sample of the analog signal generated by the ADC. And the processor, which is operably coupled to the ADC and the first buffer, transfers the first sample from the first buffer to a nonvolatile memory so as to store a digital representation of the analog signal in the nonvolatile memory. The processor also interrupts the transfer to store at least one second sample of the analog signal generated by the ADC in a second buffer operably coupled to the ADC, e.g., in response to a signal from a timer or the ADC's acquisition of a second signal.

Some examples of this embodiment also include at least one microphone, operably coupled to the ADC, to provide the analog signal representative of the measurement of the environment. These examples may include an array of microphones to provide an analog signal comprising a plurality of audio tracks.

Yet another embodiment of the present invention includes a method of recording sound in an environment subject to impulse noise characterized by a rise time less than or equal to about 50 μs. This method involves producing, with a microphone, an analog signal representative of the impulse noise, the analog signal having a bandwidth of at least about 15 kHz and a peak amplitude of at least about 180 dB. An ADC generates a first sample of the analog signal at a sampling rate equal to or greater than 40 kHz. This first sample is stored in a buffer, then written from the buffer to a non-transitory memory in a period less than or equal to about 25 μs. And the ADC generates a second sample of the analog at the sampling rate.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 2C is a block diagram illustrating the compact, portable audio recording system of FIG. 2A with balanced stereo microphones in accordance with some embodiments.

FIG. 6A is a spectrogram of frequency versus time of a single spoken sentence recorded by a high-bandwidth audio recording system in accordance with some embodiments. FIG. 6B is a spectrogram of frequency versus time of the single spoken sentence in FIG. 6A after speech removal according to the process illustrated in FIG. 5 in accordance with some embodiments.

FIG. 9B is a series of plots illustrating an implementation of the full algorithm for an impulsive noise source, with an attenuation and gain channel on the same pressure sensor, in accordance with some embodiments.

FIG. 11 is a diagram illustrating a micro-dosimeter for attachment to or implantation in a subject in accordance with some embodiments.

DETAILED DESCRIPTION

The present disclosure relates generally to systems, apparatus, and methods for recording and/or measuring time-varying acoustic pressure, including continuous noise and/or impulse noise, while retaining spectral and/or temporal information about the signal, such as rise times, peak amplitudes, and/or energy across frequency bands. Noise exposure data may be used to influence hearing protection standards, development, and training. Noise exposure data is of particular interest to government and military agencies, which use the data to better understand the effects of complex noise environments on soldiers (among others). However, access to a full spectrum and dynamic range of noise exposure histories also is of interest to consumer, medical, and occupational health industries.

Examples of the present technology include compact, portable systems suitable for recording broadband audio signals, even in rugged and hostile environments. In some cases, these systems may be small and light enough to be worn on headgear or clothing, yet store several hours of audio data acquired at bandwidths of about 10 kHz to about 100 kHz or more. The audio data collected by these systems can be used to measure a wide variety of different noise parameters, including parameters related to exposure to impulsive sounds (e.g., gunshots), for use in improving predictive modeling of potential noise-induced hearing injuries. For example, a system may be used to quantify a soldier's exposure to noise on the battlefield, a construction worker's exposure to noise at a construction site, or a factory worker's exposure to noise in a factory by recording real-time acoustic source characterization of background and impulsive sounds. Other applications include characterizing sound(s) associated with raceways (e.g., at motor sports events), spacecraft launches, pyrotechnics, logging operations, sawmills, lumberyards, demolition, construction, gun ranges, subways, trains, airplanes and airports, and emergencies (e.g., fires, shootings), etc.

The collected data can be used to develop a "transfer function" that maps environmental noise dosimetry data to standard auditory damage models. The collected data also may be used to investigate sound propagation from the body to the tympanic membrane and to assess standard auditory damage models. Sound exposure information derived from the collected data can be used to modify noise-induced hearing injury models in order to improve the ability to predict auditory damage and design optimized mitigation strategies.

Figure 1:
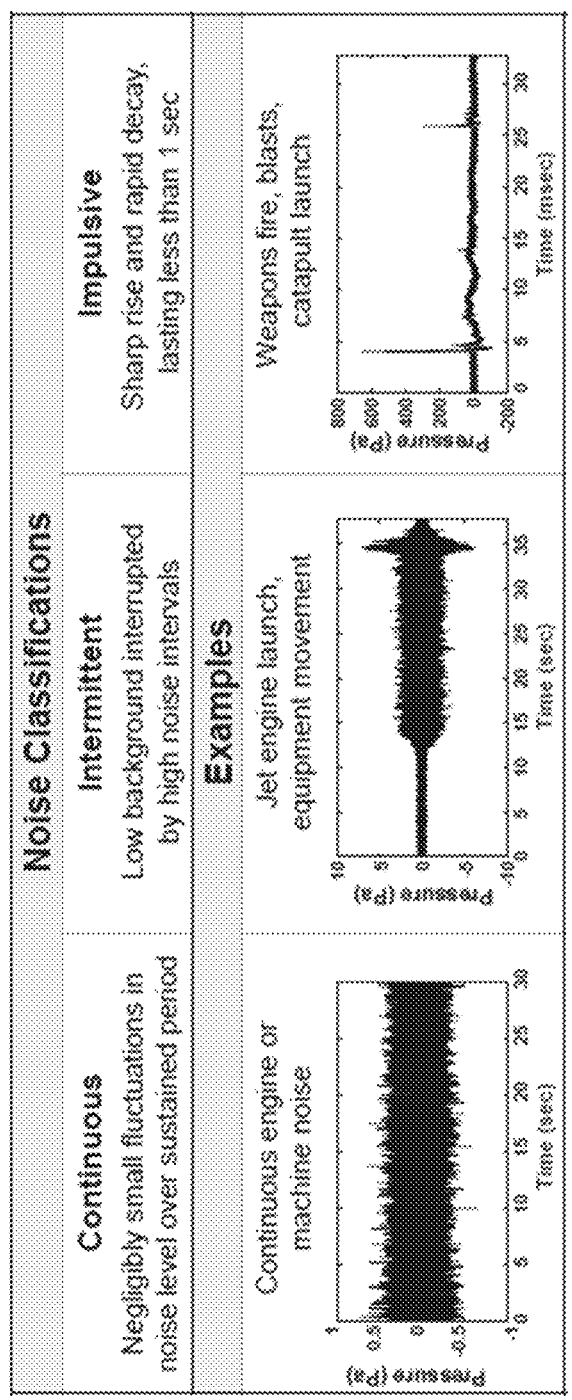
FIG. 1 is a table illustrating noise types and example waveforms in accordance with some embodiments.

To understand the needs of a dosimetry device, it can be informative to classify noise into three general types: continuous, intermittent, and impulsive, as illustrated in the table of FIG. 1, including example waveforms of each type. Of these types, impulsive noise may be the most demanding with respect to dosimeter design due to its highly dynamic nature and extreme levels, for example, from weapons fire. This challenging range of conditions drive the need for a broadband dosimetry device with a high sampling rate and a wide dynamic range to avoid clipping or distortion from large blasts. A fourth type, complex noise, combines background (continuous or intermittent) and impulsive noise, each independently contributing sufficiently high levels to induce temporary threshold shifts (TTS).

In practice, dosimetry data can be collected with free-field, on-body, or in-ear devices. Free-field noise surveys typically are short in duration (lasting no more than a few hours) and characterize the noise levels of an environment rather than for an individual. Accurately translating a free-field survey to the dose for an individual can be challenging. For example, reverberating noise within closed spaces can produce spatially varying noise levels where the perceived level at the eardrum can vary dramatically (10 dB or more) depending on the exact positioning of body and ear relative to the noise source. This variability is particularly problematic for impulsive noise, due in part to its broad spectrum. High frequency (short duration, short wavelength) components are susceptible to reflections from shorter spatial scales, resulting in reverberation and multipath that can dynamically change the noise levels observed as an individual moves or interacts with his or her environment. As a result, routine motion could result in fluctuating noise levels throughout the day. In an attempt to address this, many modern, small-form-factor commercial off-the-shelf (COTS) dosimeters can be worn on the body (preferably in close proximity to the ear) to directly measure the dose in the vicinity of an individual, but they typically lack the dynamic and frequency ranges necessary for military use.

Another key challenge in translating noise surveys to individual doses is that a dose should account for all exposure within a 24-hour period. In the absence of noise-exposure data during off-duty hours, it is typical to assume that the off-duty noise contributions are negligible, which may introduce a downward-bias on the total daily dose estimate. Furthermore, an implicit assumption of the EEH is that individuals exposed to loud noises have a recovery period following the exposure that is at least as long as the exposure duration. This quiet recovery period allows the ear to recover from TTS to normal hearing levels, and an upper limit on "effective quiet" noise levels to support TTS recovery has been estimated as 65-75 dBA. Moving toward 24-hour dosimetry is important for capturing the full daily dose of an individual and can also allow direct measurement of the recovery conditions for an individual.

Damage risk metrics are calculations or characteristics of the measured noise waveforms that quantify a harmful aspect of a noise. In conjunction with a metric, a damage risk criterion (DRC) may be defined that enforces a limit on the metric for safe noise exposure. The military and other regulating agencies set damage risk criteria that specify the conditions where hearing conservation measures are needed. In dosimetry, a common damage risk metric is a time-weighted average (TWA) of the A-weighted noise level:

$$L_{Aeq,T} = 10\log_{10}\left[\frac{1}{T}\int_T \frac{p_A^2(t)}{p_o^2}dt\right], \quad (1)$$

where T represents the exposure duration, $p_A(t)$ is the A-weighted pressure-time waveform over time T, and $p_o=20$ μPa is the reference pressure level. A common limiting criterion for this metric is 85 dBA over an eight hour period, that is, $L_{Aeq,8h} \leq 85$ dBA.

While $L_{Aeq,8h}$ has wide acceptance as a damage risk metric for continuous-noise environments, many concerns have been raised that it is not adequate for predicting hearing damage from complex or impulsive noise. One issue is that $L_{Aeq,8h}$ and other energy-based metrics ignore much of the temporal and spectral structure of the noise, yet there is evidence to suggest that some of these structural features are important in determining the severity of damage from impulsive and complex noise. For example, studies have shown that $L_{Aeq,T}$ under-predicts hearing damage when continuous and impulsive noise are combined, and other studies suggest that impulsive exposures with predominantly low-frequency energy may be less hazardous than an equal-energy impulse dominated by higher frequencies. Additionally, the linear relationship between energy and permanent threshold shifts (PTS) only holds for noise levels up to about 140 dB. Above this level, non-linear operations may be necessary to translate the energy metric into auditory damage. In response to these concerns, several complementary or alternative metrics have been proposed for impulsive noise. Table 1 summarizes several damage risk metrics that have been proposed or currently are used in hearing-conservation guidelines. An important caveat made in the new military standard, MIL-STD-1474E, is that while it defines damage risk metrics and sets permissible noise levels for the design and development of military systems, this new standard stops short of setting limits on hearing conservation requirements for military personnel. Therefore, the criteria in TABLE 1 that reference MIL-STD-1474E should not be considered as personnel dosage limits, but rather limits on the noise conditions of systems used within a military environment.

between the onset and return to baseline pressure of an impulse) and the A-duration value itself may be uncertain. A-duration calculations are well-suited for blast overpressure waveforms such as those from large munitions, but challenging to measure on small weapons in the field and may be altogether inappropriate for some impulsive noise such as the highly reverberant impact noise from an aircraft carrier catapult. Furthermore, if A-duration is overestimated as a result of one of the complications just mentioned, it can lead to the undesirable effect of under-predicting the risk of hearing damage. For example, $L_{I\,Aeq,8h}$ can be inappropriately reduced by as much as 16.5 dB for the case where the A-duration is overestimated at a value ≥2.5 ms.

The AHAAH model is an electro-acoustic model developed by the U.S. Army and calculates a value in Auditory

TABLE 1

| Metric | Reference | Criterion | Strengths | Limitations |
|---|---|---|---|---|
| TWA Noise Level ($L_{Aeq,8h}$) | MIL-STD-1474E NIOSH 1998 | 85 dBA for 8 h/ 3 dB exchange | Simple to compute Validated on human and animal studies | Neglects nonlinearities in ear May over- or under-predict risk of impulsive noise Presumes adequate recovery conditions exist |
| Peak Level ($L_{peak}$) | MIL-STD-1474E NIOSH 1998 | 140 dB | Prevent mechanical trauma to ear | Neglects temporal and energy characteristics |
| Duration (A- or B-duration) | MIL-STE-1474D (obsolete) | Varies with $L_{peak}$ | Duration with peak levels approximates energy | A-duration not meaningful for some impulses Very limited temporal characterization |
| TWA Impulse Noise Level ($L_{IAeq,8h}$) | MIL-STD-1474E | 85 dBA for 8 h/ 3 dB exchange | Simple to compute Builds on well-established $L_{Aeq,8h}$ | A-duration not valid for some impulses Limited validation |
| AHAAH ARU | MIL-STD-1474E (U.S. Army) | 200/500 ARU | Functional model of ear Models hearing protection and middle-ear reflex effects | Complex software; limited to short audio files Parameter selection unclear |
| Kurtosis | Qiu et al. (2006); Goley et al. (2011); Sun et al. (2016) | N/A | Simple to compute Correlates with PTS in chinchilla studies | Unclear how best to incorporate in metrics Limited studies with noise from real-world environments Parameter selection unclear |

Until recently, damage risk metrics for impulses focused primarily on limiting the number of impulses based on peak level and duration; however, peak level and duration have failed to show a strong correlation with NIHL for impulsive noise. Furthermore, accurate measurement of the peak and duration are often complicated by reverberation and reflections which add substantial variability to the calculated values. MIL-STD-1474E introduces two alternatives as impulse noise damage risk metrics: (1) the $L_{I\,Aeq,8h}$ metric which parallels the conventional $L_{Aeq,8h}$ calculations but is explicitly defined on a 100 ms interval around the impulse and includes a correction factor for long A-duration impulses; and (2) Auditory Risk Units (ARUs) computed from the Auditory Hazard Assessment Algorithm for Humans (AHAAH) model. Both metrics are acknowledged to have limitations and require further study, but are considered superior to the methods of the previous standard, MIL-STD-1474D.

One limitation of the $L_{I\,Aeq,8h}$ metric is that there is little validation of the A-duration correction factor (i.e., the time Risk Units (ARUs) that represents energy reaching the inner ear, i.e., basilar membrane displacement. The AHAAH model includes many software parameters, including options to activate or deactivate the non-linear middle-ear reflex that has been shown to limit susceptibility to hearing damage when a person is anticipating a loud noise. An additional strength of the AHAAH algorithm is that it has the ability to apply a transfer function to convert free-field noise measurements to their expected levels at the eardrum, with the option of including suppression effects from a number of hearing-protection devices. Having been developed as a laboratory tool, there are currently some practical considerations, however, that limit the AHAAH model's applicability for dosimetry. The software package was developed specifically to run on short excerpts (tens of milliseconds) of an impulsive waveforms and is not well-suited for evaluating ARU over extended-duration and complex noise, which may contain a sequence of impulses embedded in elevated background noise. In addition to the memory and computational complications of processing extended data records, there is no clear process for dynamically or adaptively controlling on- and offset of the middle-ear reflex where impulses may occur periodically but the state of an individual's middle ear reflex at any given time may not be known.

Several recent studies have sought to model auditory damage from complex noise exposures that may be more realistic to military and industrial settings. One concept that has shown promise is calculating kurtosis as a complement to TWA noise levels. Kurtosis is a statistical measure (fourth moment) of the data that correlates with impulsive characteristics in the noise. Goley et al. (2011) proposed a kurtosis-corrected damage risk metric:

$$L'_{Aeq,T} = L_{Aeq,T} + 4.04\log_{10}\left(\frac{\beta}{3}\right) \quad (2)$$

where $\beta$ is the kurtosis of the data. $L'_{Aeq,T}$ showed improved correlation against PTS in chinchillas compared to the uncorrected $L_{Aeq,T}$. Recently, Sun et al. (2016) proposed an alternative kurtosis-based energy metric that adaptively elevates the effective energy in impulsive noise environments and reverts to the conventional A-weighted calculation in continuous noise environments. Further study is needed to validate kurtosis-corrected $L_{Aeq,T}$ over more data sets including complex military noise environments.

Ideal design characteristics for a noise dosimeter are shown in TABLE 2, some of which are specified in MIL-STD-1474E, in accordance with some embodiments.

TABLE 2

| System | COTS[1] | MIT LL Gen 1 | MIT LL Gen 2 | Ideal |
|---|---|---|---|---|
| Sample Rate | 8 kHz | 36 kHz | 128 kHz | 192 kHz[2] |
| Data Precision | 16 bit | 16 bit | 24 bit | 24 bit[2] |
| Battery Life | 24 h | 8 h | 12-24 h | Days to Weeks |
| Measurement Range | 70-140 dBA | 70-165 dBA | 65-180 dBA | 55-180 dBA |
| Microphone Location | On body | On Helmet | Near Ear | In and/or Near Ear |
| Microphone Type | R.I.[3] | R.I.[3] | Pressure | Pressure (in-ear) R.I.[3] (near-ear) |

[1]Representative Commercial off the Shelf (COTS) noise dosimeter, ANSI (1983) class 2 sound level meter
[2]MIL-STD-1474E instrumentation specification for impulse noise
[3]Random-incidence microphone Size, Weight, and Power (SWaP) considerations also may apply to developing physiological or environmental on-body sensing devices, and are relevant here as well. With a goal of a small package suitable for an on-body or in-ear system, the trade-off typically will be with the recording fidelity (sampling rate, dynamic range) and the duration over which data can be recorded (battery life, digital memory). While there are many commercially available devices with a wearable form factor, they are focused on occupational noise hazards below 140 dB and employ relatively low sampling rates. In military environments, however, impulse noise often exceeds these capabilities. Portable commercial audio recorders are one alternative to capture high fidelity noise exposures with a calibrated microphone, but are often bulky, have many settings and cannot process noise metrics in real-time on the device. Smartphones are another possible option, and can be accurate in certain device configurations and noise environments, but the built-in microphone typically is limited to lower sound pressure levels (non-impulse noise), low sampling frequency, and a single input channel.

Figure 2A:
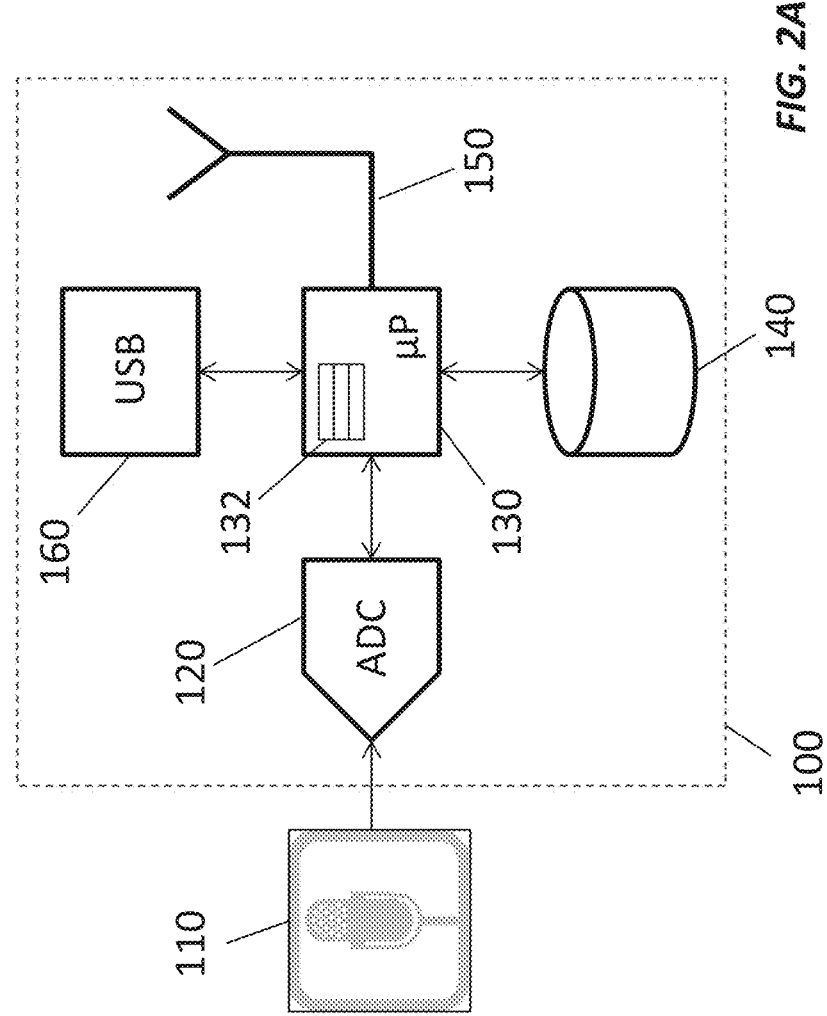
FIG. 2A is a block diagram illustrating a compact, portable audio recording system suitable for recording high-impulse sounds with a single microphone in accordance with some embodiments.

FIGS. 2A-2D illustrate a system 100 suitable for capturing, digitizing, and recording high-bandwidth audio signals with relatively large dynamic range in accordance with some embodiments. As shown in FIG. 2A, the system 100 includes an analog-to-digital converter (ADC) 120 coupled to a processor 130 (e.g., a microprocessor or microcontroller), which in turn is coupled to a nonvolatile (persistent, non-transitory) memory 140, such as a Secure Digital (SD) nonvolatile memory card or other suitable memory. In some cases, the system 100 may include one or more communications interfaces, such as an antenna 150 or a universal serial bus (USB) port 160. The system 100 may also include a power supply (not shown), such as a battery or solar cell, to power the ADC 120, processor 130, and any other electronic components.

Figure 2B:
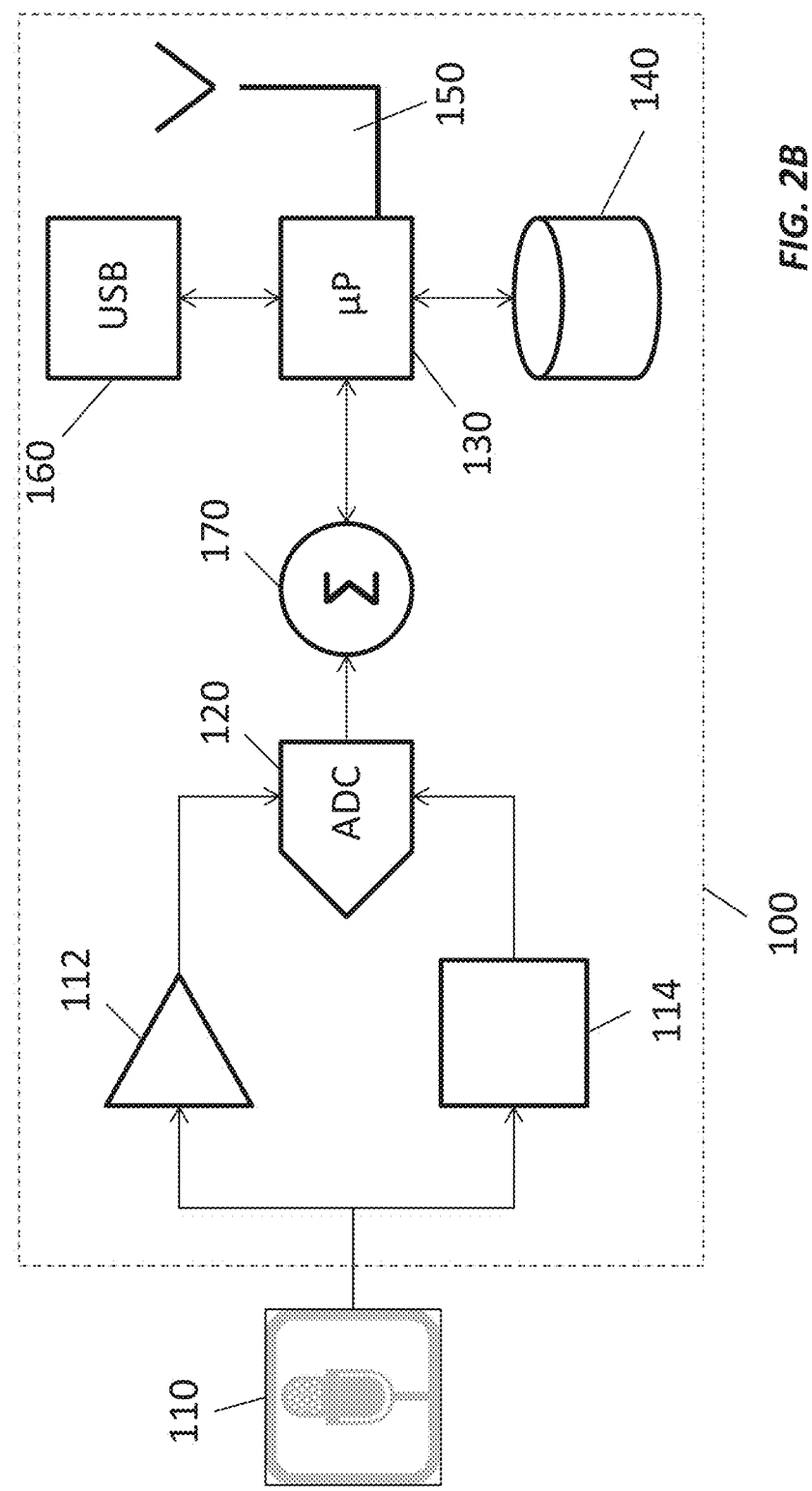
FIG. 2B is a block diagram illustrating the compact, portable audio recording system of FIG. 2A with a single microphone using balanced detection for extended dynamic range in accordance with some embodiments.
Figure 2D:
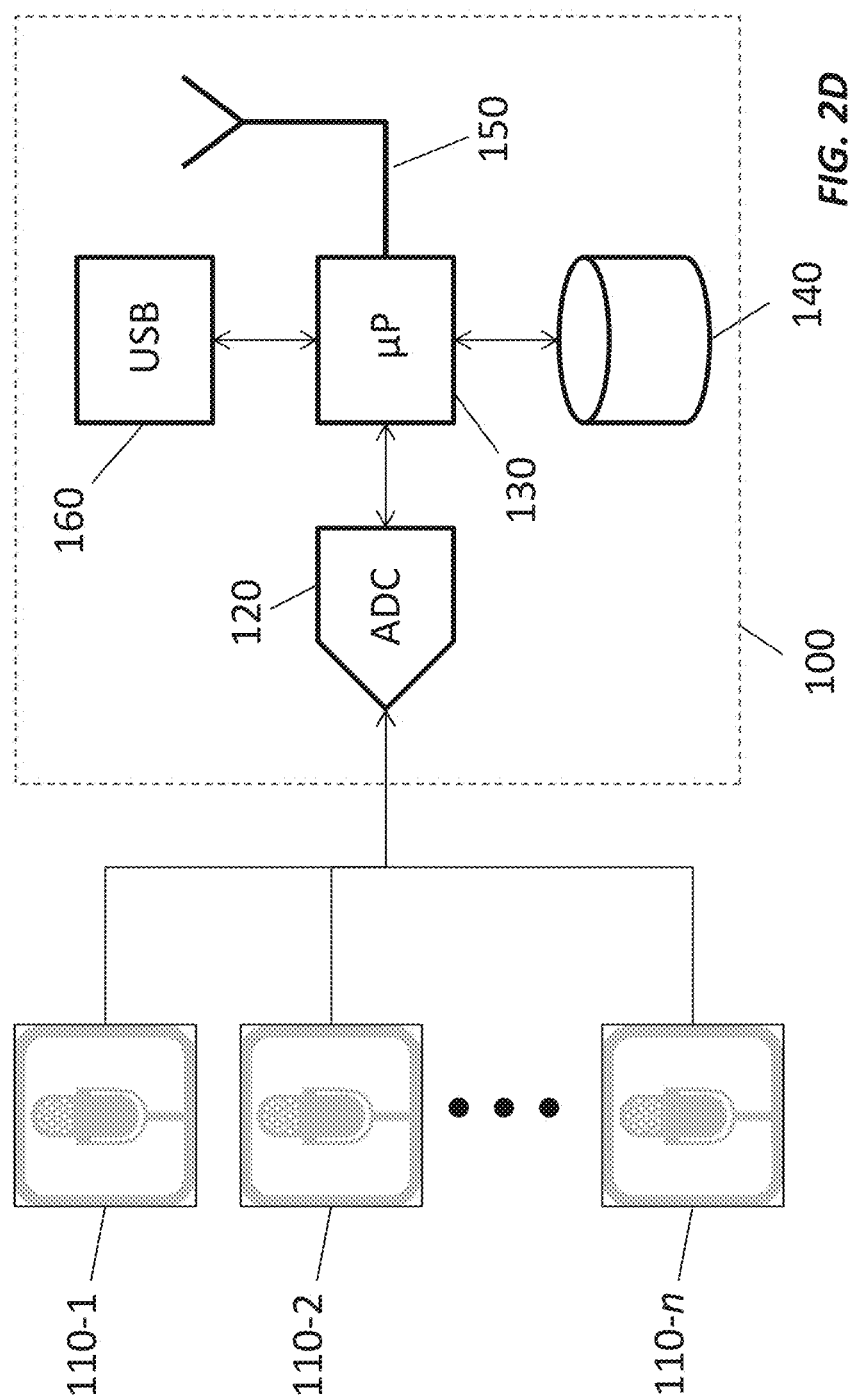
FIG. 2D is a block diagram illustrating the compact, portable audio recording system of FIG. 2A with an array of microphones to provide an analog signal with multiple audio tracks in accordance with some embodiments.

In operation, the system 100 collects analog data with a microphone 110, which captures ambient audio signals at a bandwidth of about 1 Hz or to about 50 kHz (e.g., 5 kHz, 10 kHz, 15 kHz, 20 kHz, 25 kHz, 30 kHz, 35 kHz, or 40 kHz), peak sound pressure levels of 140 dB or higher (e.g., 150 dB, 160 dB, 170 dB, or 180 dB), and at amplitude ranges of about 20 dB to about 180 dB more (e.g., 80 dB, 90 dB, 100 dB, 110, 120 dB, 130 dB, 140 dB, 150 dB, 160 dB, or 170 dB). The exact bandwidth and amplitude range of the microphone's output depends on the microphone 110 itself; different microphones may have different amplitude or frequency ranges. The system 100 also may collect audio from more than one microphone at a time, e.g., as shown in FIGS. 2C and 2D and described in greater detail below.

The ADC 120, which is coupled to the microphone's output, digitizes the analog signal from the microphone 110 at a sample rate that is equal to or greater than the Nyquist rate for the band of interest. In other words, the ADC 120 samples the analog signal at a sample rate equal or greater than twice the maximum frequency of interest in the analog signal. An ADC may operate at sample rates of about 20 kHz to about 200 kHz (e.g., 50 kHz, 60 kHz, 70 kHz, 80 kHz, 90 kHz, 100 kHz) at 16 bits or at any other sampling rate and bit level suitable for preserving high-frequency audio information captured by the microphone 110. For instance, if the analog signal extends from DC (0 kHz) to 50 kHz, then the ADC 120 samples the analog signal at rate of 100 kHz or higher to preserve the information in the analog signal. (As understood by those of skill in the art, higher sampling rates may lead to better signal fidelity.) In other cases, the low-frequency cutoff may be higher than DC, and the analog signal provided by the microphone may be mixed down to baseband to reduce the sampling rate or to improve fidelity given a fixed sampling rate.

As the ADC 120 samples the analog signal from the microphone 110, it generates individual measurements, or samples, representative of the amplitude of the analog signal at respective instants in time. (Generally speaking, the higher the bit level and sampling rate of the ADC, the better the quality of the digital data.) The processor 130 stores these samples temporarily in one or more buffers 132 before transferring them to the nonvolatile memory 140. In some cases, the processor 130 may control the sampling and data transfer according to an interrupt-driven process as explained in greater detail below with respect to FIG. 3.

The nonvolatile memory 140 stores the recorded digital data for later retrieval and processing. In some embodiments, the nonvolatile memory 140 may include removable storage media, such as one or more industrial-grade micro SD cards (class 10/90-X), that may be wholly or partially removed from the system 100. Using a memory card or other removable storage medium to store the digitized data makes the system especially useful in rugged environments: the memory card may be swapped in the field, e.g., at regular intervals or when it is full, for a blank memory card enabling only limited interruptions in data collection. And in some cases, the system 100 may store data in the buffers or in another memory card while the full memory card is being replaced to prevent loss of data.

The system 100 may also transfer data stored in the nonvolatile memory to other electronic devices, including servers or other external computers, via the antenna 150. Depending on the application, the system 100 may be wirelessly connected to a communications network, such as the internet, cellular data communications network, or local area network, via the antenna 150 using any suitable communications standard. (The system may also include an amplifier, mixer, local oscillator, or any other component suitable for wirelessly transmitting or receiving digital data.) In some cases, the antenna 150 may broadcast information about the system 100 and the captured audio data. For instance, the processor 130 may compress and transmit the stored audio data in one or more brief transmission bursts at opportunistic or preprogrammed intervals. It may also transmit the digitized audio data in real-time in addition to or instead of storing it in the memory 140. In some cases, the antenna 150 is used to save power by selectively transmitting data when desired and having the electronics enter into sleep mode when not transmitting data.

The antenna 150 also may be used to receive processing instructions, firmware updates for the processor 130, or data, such as position data from the Global Positioning System (GPS) or any other navigation system. For example, the processor 130 may store indications of the system's location derived from the position data in the memory 140 with the digitized audio information. If desired, this location information may be used in tagging or processing the stored audio information. The antenna 150 may also be used to reduce power consumption.

Alternatively, or in addition, the system 100 may transfer stored audio information to an external electronic device, such as a computing device connected to a computer network, via the USB port 160. The system 100 also may receive instructions, including processing instructions or updates for the processor 130, via the USB port 160. And in some examples, the USB port 160 may receive electrical power to power the system 100, to recharge the system's batteries (not shown), or both. Those of skill in the art will also readily appreciate that the system may include other ports (e.g., separate power ports) instead of or in addition to the USB port 160 shown in FIGS. 2A-2D.

Extension of Dynamic Range and/or Capture of Sound Source Position Information

The system's amplitude range and frequency range depend in part upon the source of the analog data—in FIG. 2A, the microphone 110. As mentioned above, the ADC's sampling rate may be selected or controlled by the processor 130 to be greater than or equal to the Nyquist rate of the highest-frequency spectral component captured by the microphone 110. Similarly, the ADC's bit depth may be selected to match or exceed the microphone's dynamic range to preserve as much of the acquired audio information as possible during the digitization process.

In some cases, the system 100 may be coupled to analog signal processing components to extend the amplitude range covered by the analog input to the ADC 120. For instance, FIG. 2B shows a system 100 coupled to a single microphone 110 via an amplifier 112, an attenuator 114, and a summing/combining node 170. Depending on the embodiment, the summing/combining node 170 may be implemented as an analog summing circuit, a mux digital summation using software code, or any other suitable implementation.

In operation, the microphone 110 converts audio-frequency vibrations into an analog electrical signal, which is coupled in parallel to both the amplifier 112 and the attenuator 114. The amplifier 112 amplifies the analog signal, e.g., with a gain of 10 dB, effectively extending the lower edge of the system's amplitude range downwards. Similarly, the attenuator 114 attenuates the analog signal, e.g., with a loss of 10 dB, to extend the upper range of the system's amplitude range. The summing/combining node 170 combines the resulting amplified and attenuated digital signals into a single digital signal whose amplitude range is larger than the amplitude range of the raw analog signal generated by the microphone 110, e.g., by an amount up to the union of the range(s) of each analog signal. In some cases, combining the analog signals may increases the signal-to-noise ratio by averaging noise common to both analog signals.

FIG. 2C illustrates how amplification and attenuation may be used with a stereo microphone system to acquire, digitize, and record stereo audio data using the compact, portable audio recording system of FIGS. 2A and 2B. In this case, the stereo microphone system includes at least two microphones 110-1 and 110-2 to detect sounds at different spatial positions. For instance, microphone 110-1 may be mounted to face left and microphone 110-2 may be mounted to face right or vice versa.

In some cases, each microphone may detect sound over a different amplitude range. For instance, the first microphone 110-1 may produce a first analog signal representative of sound power levels extending from about 115 dB to about 180 dB and the second microphone 110-2 may produce a second analog signal representative of sound power levels extending from about 75 dB to about 140 dB. In operation, the summing/combining node 170 combines the first and second analog signals to form a combined analog signal whose amplitude range extends from about 75 dB to about 180 dB.

The system 100 also may be used to digitize, record, and process audio information captured by multiple microphones. In FIG. 2D, for example, the system 100 is coupled to a microphone array that includes two or more microphones 110-1 through 110-$n$ coupled to the ADC 120. The microphones may be distributed and mounted throughout a particular environment using any suitable mounting scheme. For instance, they may be distributed about the circumference of a hard-hat or helmet and wired to the ADC 120 (possibly via one or more other active or passive electronic components). The microphones also may be distributed throughout a rugged environment (e.g., on different hard-hats or helmets, on different vehicles, etc.) and wirelessly coupled to the ADC 120 (e.g., via wireless links), with accelerometers, gyrometers, GPS receivers, or other navigational aids used to track their relative and/or absolute positions and orientations for processing and analysis.

Each microphone in the microphone array provides a separate audio signal, or track, that represents audio-frequency waves sensed by at the microphone's locations. These audio tracks may be combined (e.g., summed) to form a single analog signal that is sampled by the ADC 120 at a sampling rate equal to or greater than the Nyquist frequency of the highest-frequency spectral component. Alternatively, the ADC 120 may sample each audio track in a round-robin/interleaved fashion, e.g., first by sampling the analog signal from microphone 110-1, then by sampling the analog signal from 110-2, and so on. The system 100 also may include multiple ADCs (not shown), each of which is dedicated to one or more respective microphones in the microphone array.

In certain embodiments, the processor 130 may use multi-track audio information acquired by the microphone array to estimate the relative location of the source of a particular sound or to identify different types of sounds. For instance, the processor 130 may use stereo or multi-track audio information to distinguish a blast or gunshot from a signal caused by dropping a microphone on the ground. Post-processing also may be used to identify sounds and their locations. If desired, the audio track from a microphone may be amplified, attenuated, and/or delayed using the appropriate analog components placed in series with the microphone in the microphone array to extend the dynamic range, increase sensitivity, etc., as described further herein.

Interrupt-Driven Processing Modes

As mentioned above, the system 100 shown in FIGS. 2A-2D may operate in interrupt-driven processing modes to improve sampling consistency, reduce power consumption, and reduce interference between writing data to memory and sampling the analog signal. In one mode, the system uses a timer, such as a software timer implemented in the processor, to interrupt data transfer from the buffer(s) to the nonvolatile memory during each sampling operation by the ADC. In another mode, the ADC interrupts the data transfer each time it generates a new sample. Depending on the implementation, the system may be hard-wired to operate in either the timer-driven interrupt mode or the ADC-driven interrupt mode or configured to switch between the two.

Figure 3:
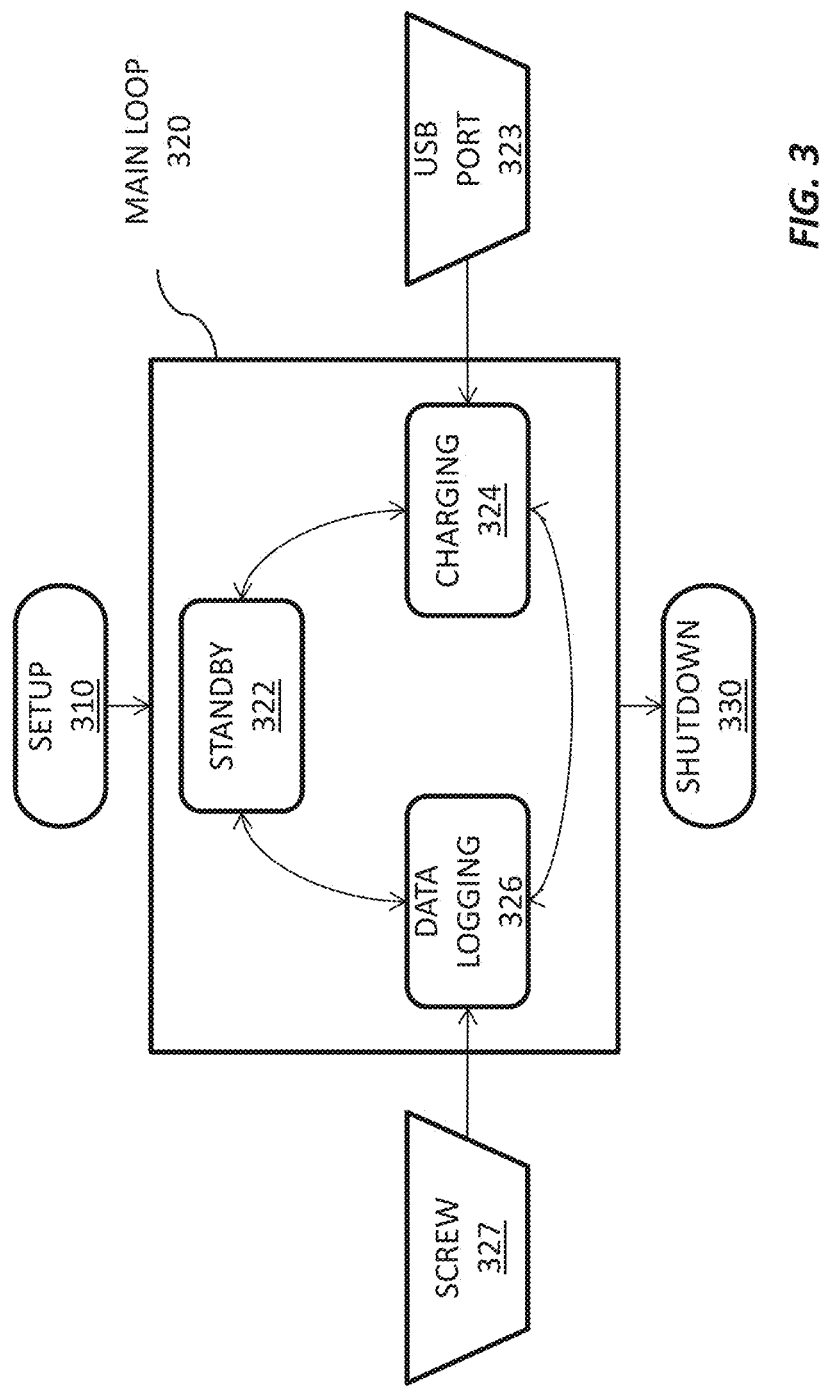
FIG. 3 is a flow diagram illustrating interrupt-driven processing based on a timing signal employed by a compact, portable audio recording system in accordance with some embodiments.

FIG. 3 illustrates a process 300 with sub-processes and functions common to the timer-driven interrupt mode and the ADC-driven interrupt mode. In both interrupt modes, the system 100 executes a setup function 310, then a main loop 320 for logging data and performing other functions. The setup function 310 is executed once the device is powered on and may include assigning the input and output pins on the microprocessor, initializing the system's identification (ID) number (e.g., for using multiple devices), setting the analog-to-digital conversion resolution (e.g., to 16 bits), and creating a file in the nonvolatile memory to receive the digitized data from the buffer(s). In some examples, the ADC resolution may switched "on the fly" among different settings, e.g., to any bit level from about 8 bits to about 24 bits. For instance, switching to a higher resolution increases data fidelity, and switching to a lower resolution may increase battery life, decrease processing time, and make more conservative use of storage capacity.

Once setup 310 is complete, the system enters the main loop 320 and executes this main loop 320 repeatedly until the system is powered down (e.g., turned off by the user) as part of a shutdown function 330. In some implementations, the main loop 320 includes a large case/switch statement in which the system switches among different states in response to various user actions, like plugging the device into a computer or screwing in the magnetic screw. These states include a standby state 322, a charging state 324, and a data logging state 326. The processor may call different functions in each state, depending on user input, remaining battery charge, environmental conditions, etc.

In the standby state 322, the system waits to be connected to a computer to download data and/or charge, or for a user input 327 that causes recording to begin, such as screwing in a magnetic screw as described further below. While in the standby state 322, the processor may call functions that check for a USB connection or other connection to an external computer, for the battery voltage level (e.g., with respect to a "turn-off" threshold), and for user input 327 that (e.g., as indicated by a changed in voltage from a Hall effect sensor that senses the position of a magnetic screw).

The system enters the charging state 324 when it is connected to a computer or other electronic device, e.g., by plugging a cable into its USB port 325. Once the system is connected to the computer, it switches into a "reader mode" in which the contents of the nonvolatile memory (e.g., an SD card) may be accessed from the computer. Once in this mode, the system calls the appropriate functions to monitor the charging of the battery. The system stops charging if the battery temperature increases above a threshold temperature (e.g., set to prevent battery failure), the battery voltage reaches a voltage threshold, or the battery has been charging for more than a predetermined period (e.g., a few hours). These failsafe measures may prevent the battery from charging incorrectly or exploding.

In the charging state 324, the processor may call functions that return the battery temperature (e.g., in degrees Celsius or Fahrenheit), calculate the battery voltage, and return the battery voltage. Other functions, typically used in debugging, may print the battery's voltage, temperature, or both. The processor may also call functions that initialize internal variables to monitor battery charging and that monitor the battery's voltage and temperature during charging. And the processor may check for the USB connection.

In addition, the processor may turn off and on the power to the nonvolatile memory (SD card) in the charging state 324. This enables the system to switch from a mode in which the processor may log data to the nonvolatile memory to another mode in which the nonvolatile memory may be viewed from the computer as a data drive. This function is called once the device has been connected to the computer via a USB port or other connection. Another function enables the nonvolatile memory to be viewed from the computer as a data drive. The processor may execute yet another function in which the nonvolatile memory is "ejected" from the computer, allowing the processor to access the nonvolatile memory for writing purposes.

Actuating the device, e.g., by throwing a switch or screwing a magnetic screw (step 327), causes the system to enter the data logging state 326. In response, the processor reads the system's configuration file and selects the appropriate data acquisition mode, e.g., full-resolution audio acquisition mode or low-resolution dosimeter mode. Once the processor has selected the data acquisition mode, it executes a data logging function in which it writes the data from buffers that are full to the nonvolatile memory.

Generally, the period taken the write data from a given buffer to the nonvolatile memory is less than the sampling period (the reciprocal of the sampling rate). In some cases, the buffer size is chosen to match the page size of the nonvolatile memory to reduce the amount of time required to write the data from the buffer to the nonvolatile memory. For example, the buffer size may be about 512 bytes, which matches the page size of certain SD cards. Because the buffer size matches the SD card's page size, the processor may write the data to the SD card in contiguous chunks (e.g., one page at a time), which tends to be faster than splitting the data into fragments and writing the fragments to non-contiguous portions of the SD card.

The processor continues to loop, checking to see if any buffers are full, until the magnetic screw is unplugged, the battery dies, or another signal stops execution of the data logging function 326. Unscrewing the magnetic screw or throwing the switch again causes the system to enter the standby state 322, and connecting the system to a computer may cause the system to enter the charging state 324. Upon exiting the data logging state 326, the processor closes any files open in the nonvolatile memory and returns to the main loop 320 to change states.

If the processor senses that the battery voltage is about to fall below a certain threshold voltage (e.g., 3.3 V) or the battery dies, the device stops recording and shuts down (shutdown state 330). In some cases, this threshold voltage may equal to or greater than the voltage needed to write to the nonvolatile memory. The system may remain in the shutdown state 330 until power is disconnected and reconnected.

In data sampling and logging with timer- and ADC-based interrupts, the processor executes a data logging loop in which it checks to see whether or not it has filled the buffers with data generated by the ADC. If a particular buffer is full, the processor writes the data from that buffer to the nonvolatile memory, leaving some buffer space free to hold samples collected by the ADC during the data transfer from the buffer to the nonvolatile memory. If no buffer is full, then processor waits before checking the buffer status again until the user switches the system to standby mode or charging mode, the battery dies, or the processor receives an interrupt signal from a timer or the ADC.

To interrupt the data logging process using a timer interrupt, the processor maintains a timer that counts clock ticks from a clock running at a clock rate (e.g., 48 MHz) faster than the ADC's sampling rate (e.g., 35 kHz). The clock drives the ADC by effectively setting the sampling rate to a fraction of the clock rate: when the timer reaches a predetermined threshold, the processor initiates an ADC sample collection. It also interrupts the data logging process and resets the timer, e.g., immediately after the timer overflows. Once sample collection is complete, the processor resumes the data logging process by storing the sample in a buffer and returns to the interrupted buffer checking or data writing step. When the timer overflows again, the processor initiates the next ADC sample collection, interrupts data logging, resets the timer, etc. The frequency of the timer interrupt (and hence the sampling rate) may be varied by changing the clock rate or timer threshold. For instance, the ADC sampling rate may be relatively low (e.g., about 1 Hz) for collecting low-resolution noise dosimetry data and relatively high (e.g., about 100 kHz) for collecting high-resolution audio data.

The ADC-driven interrupt approach uses sample collection rather than an external clock to trigger interruption of the data logging process. In this approach, the clock initiates a first ADC callback to start sampling. After the first callback, the ADC asynchronously initiates an interrupt after collection of each sample. In other words, the ADC samples the analog signal at the sample rate and interrupts the data transfer from the buffer(s) to the nonvolatile memory when it generates a sample. After the processor writes the sample to a buffer, the data transfer process resumes as in the timer-driven approach. Hooks in the code handle anomalies associated with the nonvolatile memory, e.g., such as when shifting from a USB reader to internal writing. Another hook detects whether or not the user has switched the system out of data logging mode, e.g., by checking for a magnet close enough to trigger the Hall effect sensor (on/off sensor) as described further below. Depending on the implementation, the ADC-driven interrupt approach may support higher sampling rates than the timer-driven interrupt approach. In addition, an external ADC suitable for supporting the ADC-driven interrupt approach may consume less power than a microprocessor used to maintain a software timer for the timer-driven interrupt approach.

Impulsive Sound Measurements

Figures 4A, 4B:
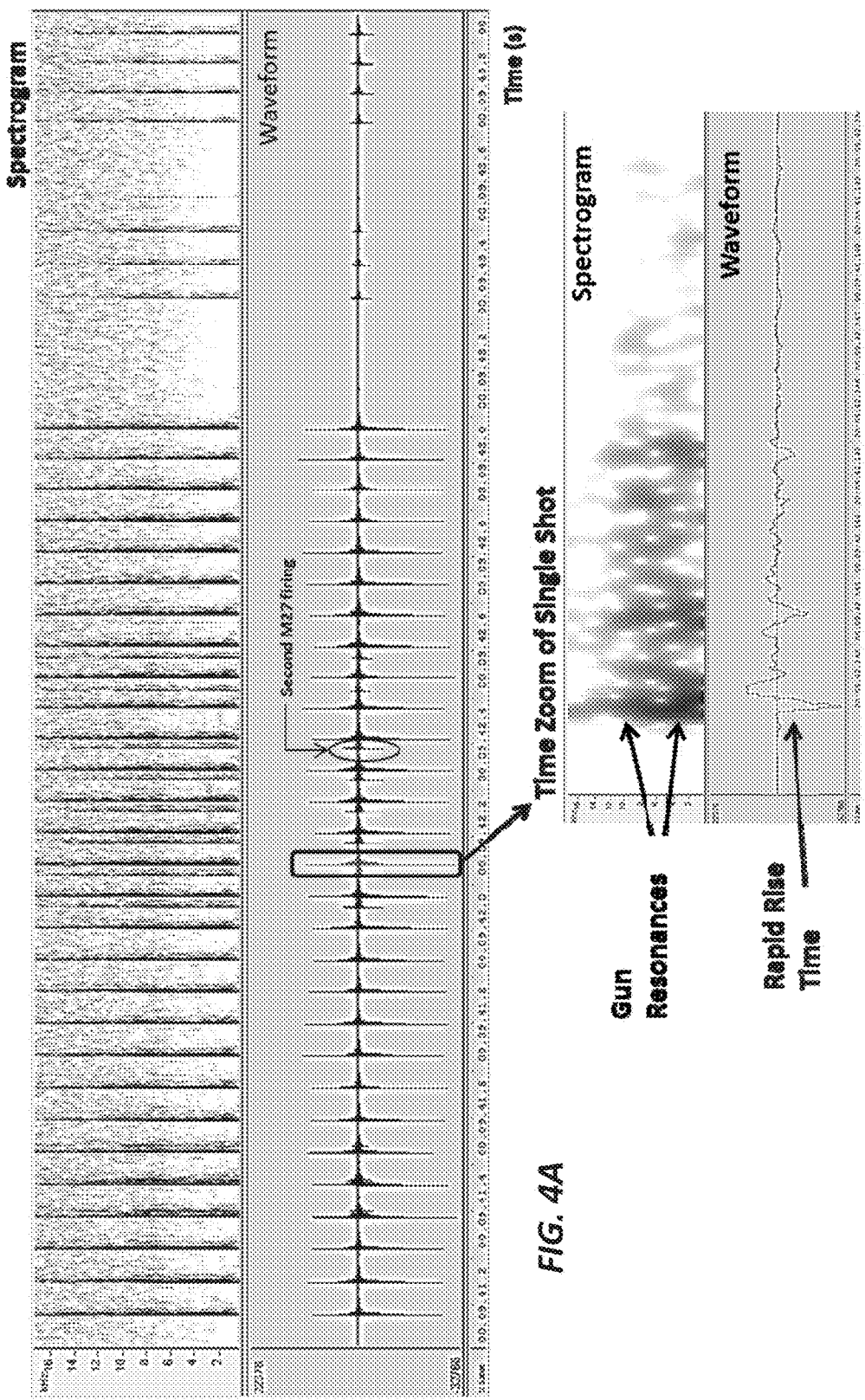
FIG. 4A is a spectrogram of frequency versus time and a plot of amplitude versus time illustrating a recording of automatic rifle fire captured using a high-bandwidth audio recording system in accordance with some embodiments.
FIG. 4B is a magnified view, corresponding to a single gunshot, of the spectrogram of frequency versus time and the plot of amplitude versus time in FIG. 4A in accordance with some embodiments.

FIG. 4A shows a spectrogram (top) and a plot of sound amplitude versus time (bottom) of gunshots from two M27 Infantry Automatic Rifles firing at 14 rounds per second captured by an audio recording system. FIG. 4B shows close-ups of the spectrogram (top) and waveform (bottom) shown in FIG. 4A; these close-ups correspond to a single gunshot. To capture the gunshots, the system acquired sound with a pair of balanced microphones like those shown in FIG. 1C over a bandwidth of about 17 kHz and digitized the resulting analog signal at a sampling rate of about 34 kHz. The "low-channel" microphone acquired sound pressure levels of about 80-140 dB, and the high-channel microphone acquired sound pressure levels spanning about 110-170 dB.

The spectrogram and the plot in FIG. 4A both show large peaks associated with gunshots from the first M27 interleaved with intermittent smaller peaks form a second M27 that is farther from the microphone. The maximum recorded sound pressure level is about 148 dB. The spectrogram shown in FIG. 4B shows the power spectral density associated with a single gunshot. And the plot in FIG. 4B shows that rise time of the resulting digital signal is less than 60 µs.

Speech Content Removal

If desired, the processor may irreversibly blur or scramble at least a portion of the acquired audio data without removing spectral or temporal information associated with the impulsive sounds. In other words, the processor may permanently remove information in one or more sub-bands of the acquired audio data without substantially affecting the ability to measure the temporal, spectral, and amplitude characteristics of impulsive sounds. For instance, the processor may remove speech content from the digital data stored in the nonvolatile memory, e.g., to minimize operational security risks on battlefields and other hostile environments, to preserve confidential information, or to meet non-disclosure obligations. This processing effectively "washes" out the phonetic and thus syllabic structure of speech, while retaining much of the temporal and spectral information used for noise induced hearing loss (NIHL) modeling, including impulsive-like sounds (e.g., gun shots and explosions) and steady and repetitive background sounds (e.g., vehicle and machine noises). Speech content and information in other sub-bands also may be removed during post-processing after the data is transferred from the nonvolatile memory to another computer or computing device.

Figure 5:
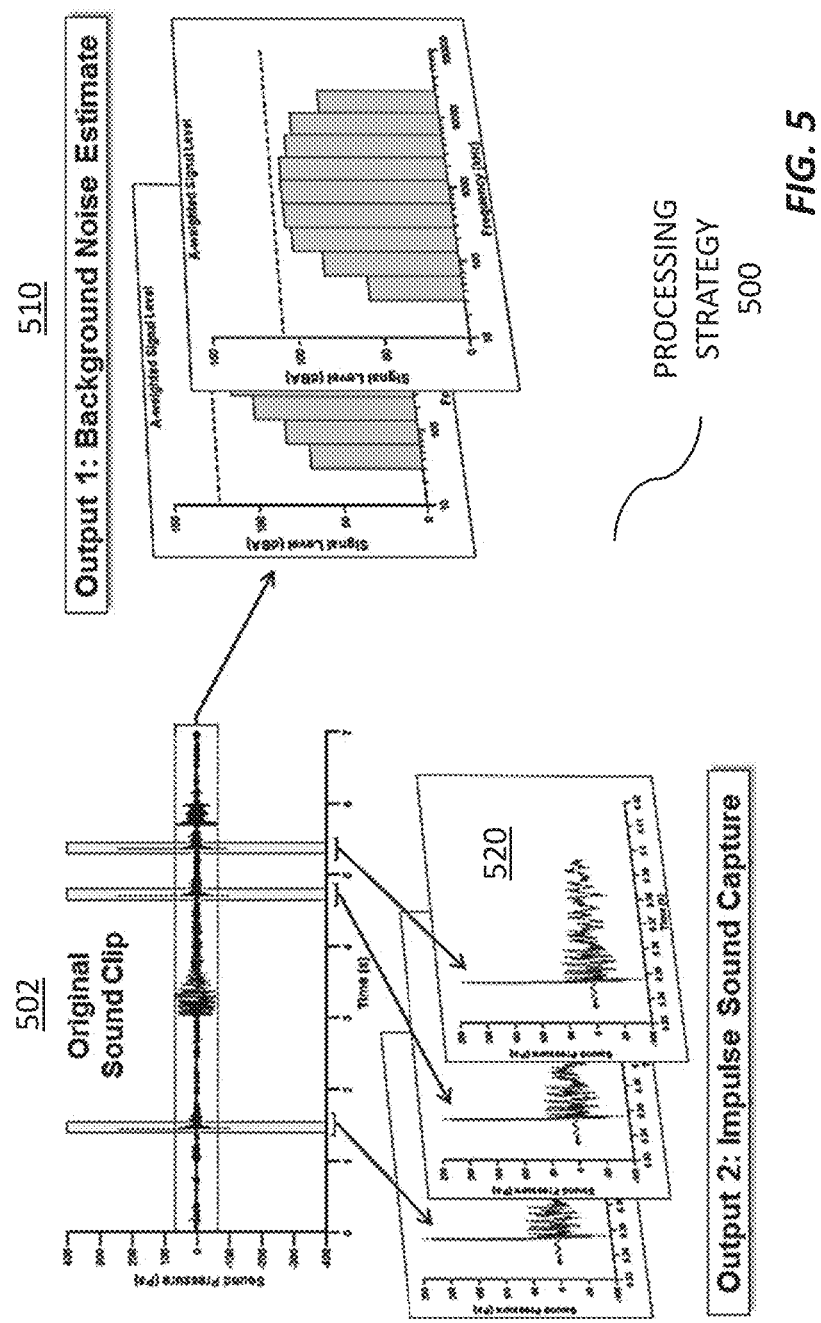
FIG. 5 is a diagram illustrating signal processing for removing speech or other information while preserving impulse information from the signal captured by a high-bandwidth audio recording system in accordance with some embodiments.

FIG. 5 illustrates a processing strategy 500 suitable for removing speech content or other information from a digitized audio sample while preserving background noise levels and impulsive sounds. The system's processor (not shown) splits an original sound clip 50, which may be stored as one or more digital samples in either the system's buffer or the nonvolatile memory, into two outputs: a first output 510 that represents a background noise estimate, and a second output 520 that represents recorded impulse sounds. If desired, these outputs may be recorded directly on the nonvolatile memory to prevent the system from recording speech content (or other information) in the nonvolatile memory.

To generate the first output 510, the processor calculates the energy in 32 logarithmically spaced frequency bands. This energy is sampled over a time interval of 200 ms, resulting in a downsampling of both time and frequency. This process of calculating the spectral energy distribution and temporal downsampling is roughly analogous to the blurring out of a person or face on television. In addition, the process of generating the first output 510 is lossy such that the first output 510 cannot be inverted to recover speech content.

The first output 510 may be generated using other frequency spacings, including logarithmic spacings, linear spacings, octave spacings, and fractional octave spacings, and other sampling intervals. Depending on how many frequency bands used and the time-averaging window, however, it may be possible to reconstruct a comprehensible estimate of the original speech waveform. But selecting downsampling parameters for the "blurring" process using perceptual and objective measures results in a first output 510 with enough spectral and intensity information to inform a NIHL model, but not enough to understand speech in a reconstructed signal.

The processor generates the second output 520 by filtering out samples whose amplitude falls below a particular amplitude threshold and/or whose duration exceeds a particular duration threshold. Depending on the application, the amplitude and duration thresholds may be chosen to capture impulsive noise events. To remove speech content but not gunshots, for example, the processor filters out samples corresponding to sound pressure levels below about 125 dB, which is louder than the loudest sound produced by a single human voice, and durations longer than about 40 ms to about 70 ms. Because a single human voice cannot produce sound this loud, the second output 520 does not include conversational human speech. Rather, it includes very loud impulsive sounds, such as weapons fire, blasts, etc. Like the first output 510, the second output 520 is generated via a lossy process and does not include any recoverable speech content.

Even if a single sample in the second output 520 includes both speech and very loud impulsive sounds, it may be difficult to separate and recover the speech for at least two reasons. First, capture of the waveform would be only about 40 ms to about 70 ms long, which is half the duration of a typical speech sound (less than the length of a single word). Second, because an impulsive sound such as gunfire is so much louder than speech (even shouting), the signal-to-noise ratio of the recording devices would likely prohibit hearing or separating the much softer speech from the gunfire.

Those of skill in the art will readily appreciate that processing strategy 500 illustrated in FIG. 5 may be used to remove other information instead of (or in addition to) speech content. For example, the second output could be generated by removing very loud impulsive sounds (e.g., sounds with amplitudes over 125 dB and durations of less than about 70 ms). Similarly, the frequency and time bins selected to generate the first output 510 may be selected to blur low-frequency mechanical sounds without unduly affecting speech content.

FIGS. 6A and 6B show spectrograms of single spoken sentence before and after processing, respectively. Both spectrograms show the temporal evolution of spectral energy of the processed signal, where red indicates higher energy and blue less energy. And the pixelation in FIG. 6B shows that processing permanently removes speech content information from the signal.

The performance of the processing strategy 500 shown in FIG. 5 was tested with a perceptual pilot test to identify words and sentences after the speech removal process. The test material included recordings of five phonetically and syllabically balanced spoken sentences with a quiet background, and recordings of five similar spoken sentences with electronically added weapons fire. These recordings were processed using the processing strategy illustrated in FIG. 5 before being interpreted by four test participants, three of whom were experts in speech and acoustic analysis. The test participants were permitted to listen to each sentence as many times as desired and instructed to write down any words they perceived.

Although the test participants were able to guess at the words in each processed recording, they indicated that they had very little to no confidence in their answers. Overall, the participants identified about 1% of the key words in the quiet environment and about 0% of the words with weapons fire. (The participants' ability to identity about 1% of the words in the quiet recordings does not mean that the speech was comprehensible because the words in the selected sentences are commonly used and it is possible to guess correctly.) These results demonstrate that even someone with extensive knowledge of sound and speech would be unlikely to interpret speech in a file processed using the speech removal algorithm.

Figure 7A:
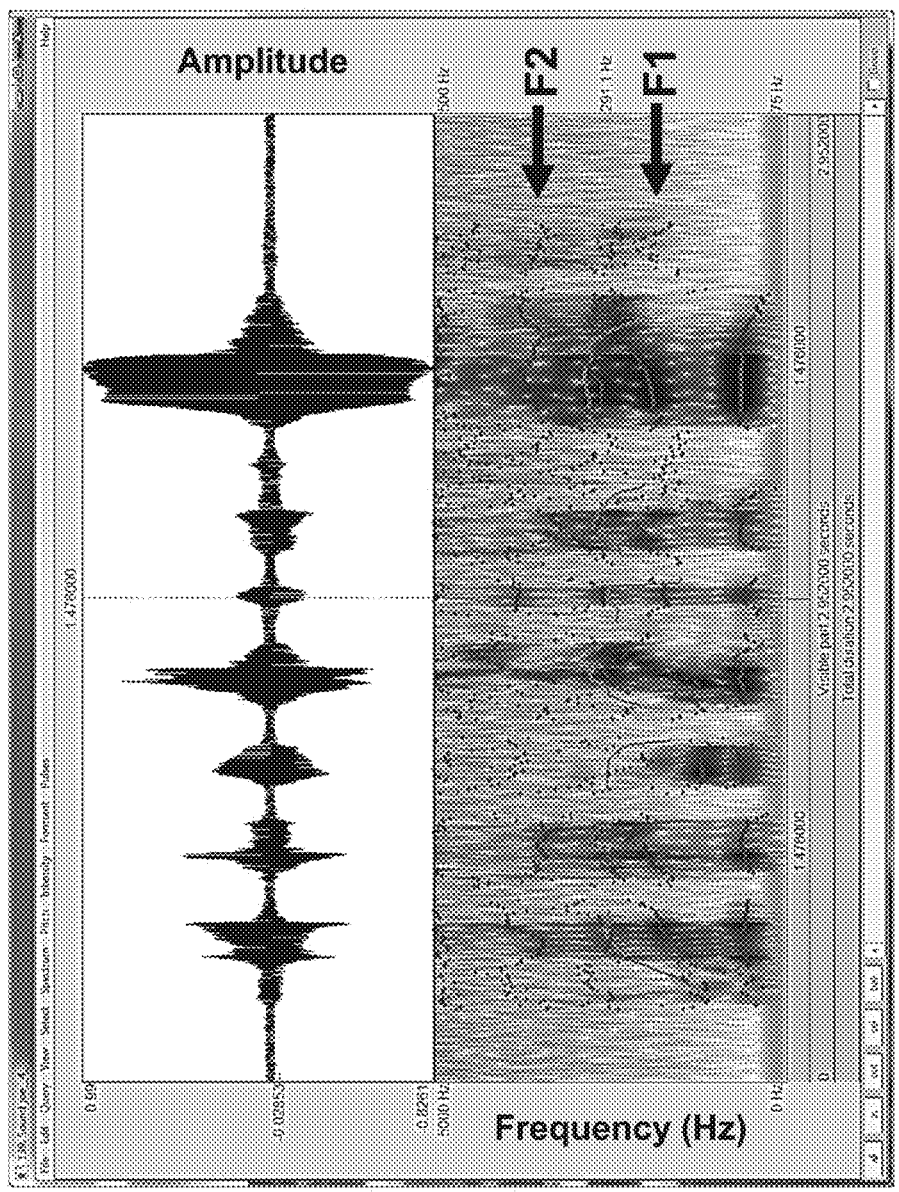
FIG. 7A is a plot of amplitude versus time and a spectrogram of frequency versus time of an original speech waveform with formant tracks and a pitch track recorded by a high-bandwidth audio recording system in accordance with some embodiments.
Figure 7B:
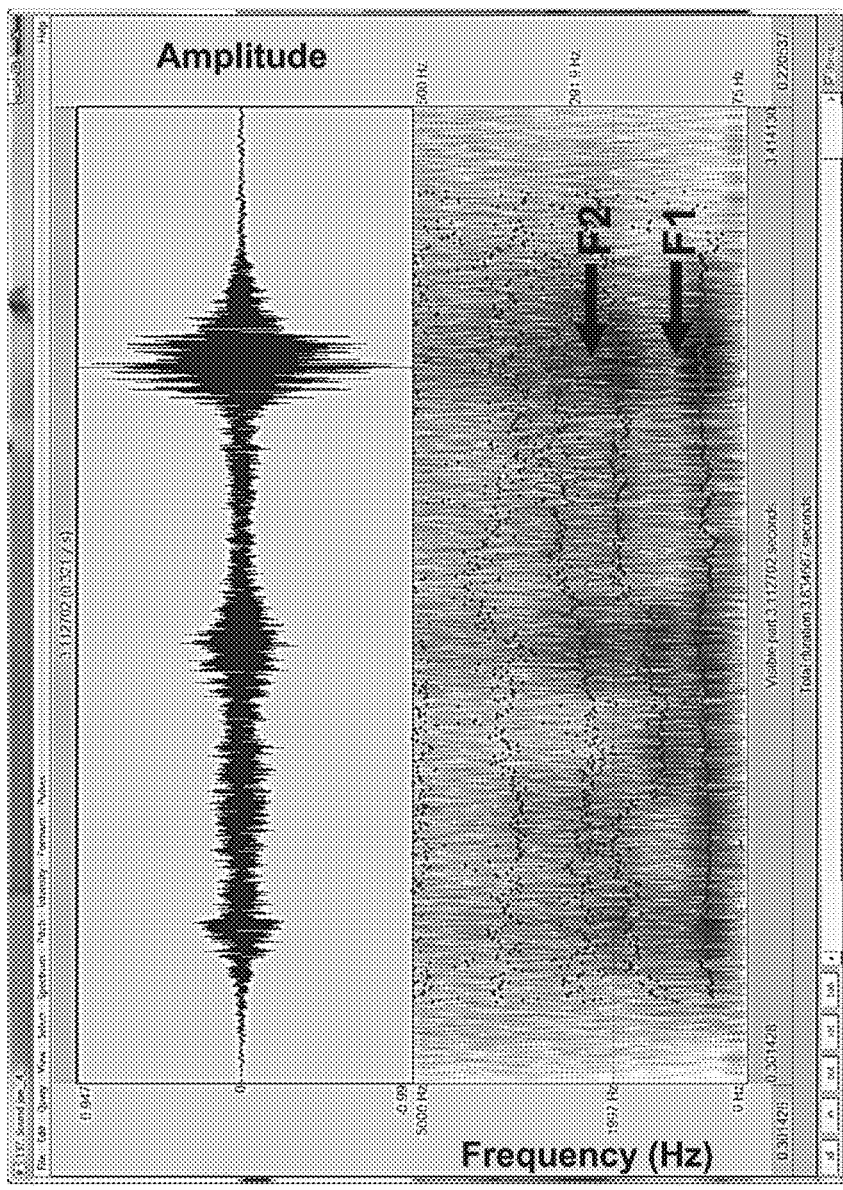
FIG. 7B is a plot amplitude versus time and a spectrogram of frequency versus time of a re-synthesized speech waveform with formant tracks and a pitch track generated from the original speech waveform depicted in FIG. 7A in accordance with some embodiments.

FIGS. 7A and 7B illustrate an analysis of processed speech that quantifies the ability to segregate vowels automatically (e.g., using a computer). FIG. 7A shows the temporal waveform (upper plot) and spectrogram (lower plot) associated with an unprocessed speech signal. FIG. 7B shows the temporal waveform (upper plot) and spectrogram (lower plot) of the same speech signal after the processing described above. Both spectrograms include red lines indicating vocal tract resonances (referred to as formants in the speech community) F1 and F2 and blue lines indicating pitch tracks estimated using a phonetic analysis software tool (e.g., Praat computer software, available from www.praat.org).

FIGS. 7A and 7B show that if vocal tract resonant structure is not present in the speech signal, then recognition by computer (or human) may not be possible. This is because the lack of vocal tract resonant structure implies a removal of phonetic and thus syllabic structure of speech. Comparing FIGS. 7A and 7B shows that the original speech signal (FIG. 7A) contains dynamic formants F1 and F2 that vary during the voiced (vowel) segments of the speech (indicated by darker horizontal bands in the spectrogram). The time variations are required in phonetic and syllabic identity. The processed speech in FIG. 7B, on the other hand, shows very noisy and inaccurate estimates of the formants, which barely vary for the different vowels across the sentence.

Using a database of 540 English vowels over 45 speakers gives more insight into how processing removes formant information. In the unprocessed speech, the different groupings are somewhat separated by their F1 and F2 formants, and are therefore fairly distinguishable from one another, which is not necessarily the case in the processed speech. This helps to explain why the test participants had trouble identifying words in the perceptual test. Using a k-means clustering algorithm to classify each vowel in the database resulted in a 56% classification rate in the unprocessed speech, while only 19% after processing. This decrease in clustering accuracy is a direct result of the information lost permanently by the processing scheme, and gives a relative metric of how much formant information is lost.

Distinction of Impulse Noise Via an Inertial Measurement Device

Inadvertent physical contacts, shocks, or tremors between a microphone and matter (e.g., wind or the brushing of a tree branch against a helmet-mounted microphone) may be mistaken as impulse noise, for example, on a battle field. A "false impulse signal" can pollute and may inevitably interfere with a noise exposure calculation. In some embodiments, an inertial measurement device (IMU), such as a tri-axial accelerometer, may be co-located with a microphone to account for false impulse signals from physical contacts with the microphone. For example, a physical shock to the helmet or body can be treated as an impulse thereby interfering with a noise exposure calculation. Using a tri-axial accelerometer as a "truth sensor," some embodiments may require no or a low acceleration response from an accelerometer to determine that a recorded impulse signal represents actual impulse noise. For example, embodiments with this augmentation may mitigate false impulse signals in the rain from rain drops continuously hitting the microphone.

Figure 8:
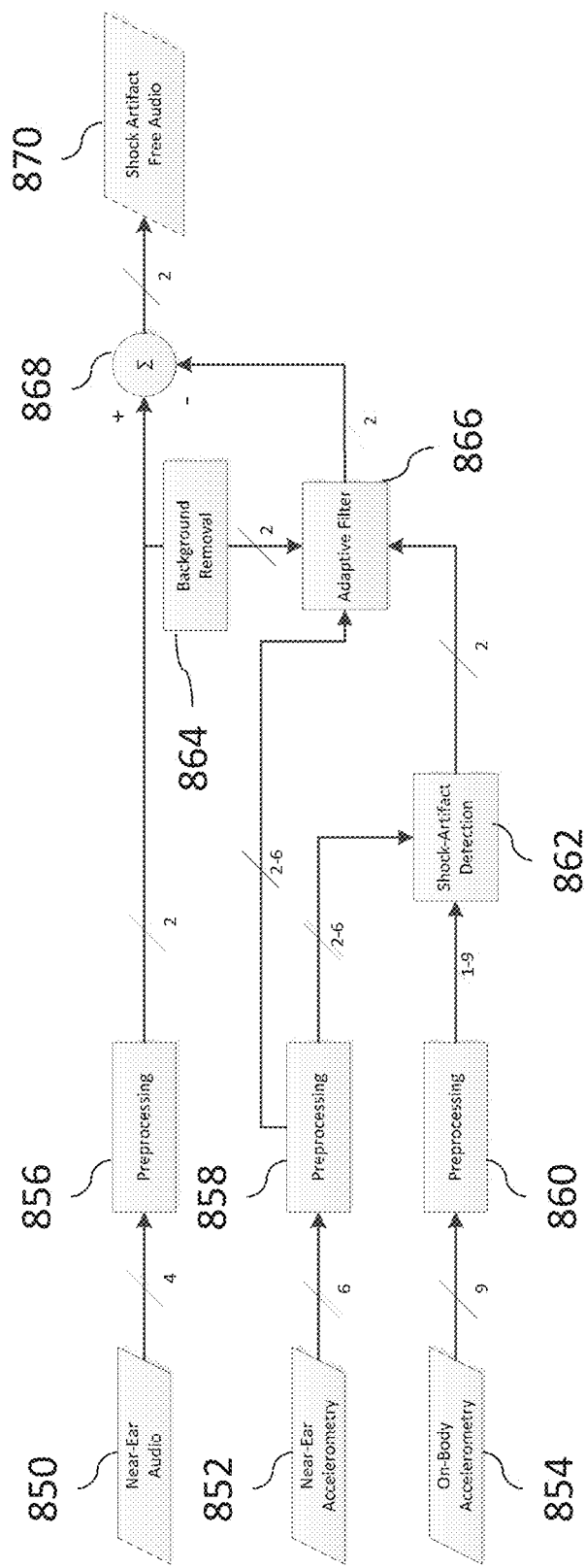
FIG. 8 is a block diagram illustrating the accelerometer false impulse rejection model in accordance with some embodiments.

FIG. 8 is a block diagram illustrating the accelerometer false impulse rejection model in accordance with some embodiments. Three time-synchronized data streams may be retained from a single dosimeter, including near-ear audio data 850, near-ear accelerometry data 852, and on-body accelerometry data 854. The near-ear audio data 850 may include two gain channels of audio from at least one and/or each near-ear microphone in the dosimeter. The near-ear accelerometry data 852 may include tri-axial accelerometry data from at least one and/or each near-ear accelerometer in the dosimeter. The on-body accelerometry data 854 may include 9-channel accelerometry data from at least one and/or each IMU located in body-worn electronics housing. Audio data preprocessing 856 may include removing DC offset and combining gain channels. Accelerometry data preprocessing 858, 860 may include removing DC offset and resampling to match the audio sampling rate. Additionally, accelerometry data may be high-pass filtered to remove low-frequency components associated with typical human motion and filtered to combine the tri-axial signals. Shock-artifact detection 862 may include analyzing time frames of the preprocessed accelerometry data for presence of possible shock artifacts. Candidate shock artifact frames may be identified using a threshold on the filtered signal or a threshold on cross-correlated data streams (e.g., left ear accelerometer vs. right ear accelerometer or left ear accelerometer vs. left ear audio). Frequency-selective background noise removal 864 may be applied to the audio channels to isolate shock-like noise from continuous background noise. The background-removed audio signal may be fed into an adaptive filter 866. For candidate frames where a shock artifact is detected, adaptive filter weights may be trained to transform the on-ear accelerometry data to match the background-removed audio signal which potentially contains shock artifacts. The adaptive filter weights may combine current and delayed time samples to predict audio response induced by a physical shock. The output of the adaptive filter 866, which estimates the audio shock artifact in a candidate frame, is subtracted from the audio channels at node 868 to produce shock-artifact free audio 870.

Calibration of Noise Levels Via an Altimeter and/or Barometer

Noises, both impulsive and continuous, are pressure waves that can be influenced by environmental conditions. Knowledge of the air pressure level, which can fluctuate over hours to days, in an environment is important in order to accurately calculate the sound pressure level. By using or including an on-board altimeter device (for measuring barometric pressure), along with a temperature and humidity sensor, some embodiments can determine the air pressure in the surrounding environment. The air pressure, temperature, and humidity measurements may be fed, in real-time, to the sound pressure level (SPL) calculation to better gauge noise levels. By taking into calculation the base-level pressure, temperature, and humidity changes due to altitude or otherwise differing noise environments, the SPL calculation then may be calibrated properly regardless of the environment or fluctuations within a particular environment over time.

Dynamic Range Extension Via Channel Combination

A dosimeter system may be designed to have a high dynamic range. In some embodiments, an analog signal (e.g., from a single microphone) may be passed through a first amplifier with gain and a second amplifier with attenuation before digitization. In other embodiments, two sensors (e.g., two microphones) may be used, the first sensor with higher sensitivity and the second sensor with lower sensitivity to span a broader range. For example, the second sensor may be a piezoelectric-type pressure sensor that captures high pressure levels up beyond 50 PSI (for capturing, e.g., blast levels). The two analog signals are then digitized separately.

In some embodiments, optimum gain matching factor $\in_{max}$ minimizes the least squares difference between two channel arrays:

$$\min_{\in}\left\{\sum_n [(g[n] - \langle g \rangle) - \in (f[n] - \langle f \rangle)]^2\right\}, \quad (3)$$

where g[n] and f[n] are the two arrays following the ADC conversion step, and $\langle \cdot \rangle$ denotes the mean over the array elements. This represents the most general form of the gain-matching factor, and may be applied to any continuous subset of the full arrays. The size of the subsets may be selected based on the desired frequency response for the gain-matching factor.

Without loss of generality, the following variables may be defined as:

$$g'[n] \equiv g[n] - \langle g \rangle \quad (4)$$

$$f'[n] \equiv f[n] - \langle f \rangle \quad (5)$$

$$R \equiv \sum_n [g'[n] - \in f'[n]]^2 \quad (6)$$

The optimum gain matching factor $\in_{max}$ is found by minimizing R, the least squares difference between the two arrays, in the following manner:

$$\frac{\partial R}{\partial \in} = \sum_n 2(g'[n] - \in f'[n])(-f'[n]) \quad (7)$$
$$= -2\sum_n g'[n]f'[n] + 2\sum_n \in f'[n]^2$$

Thus, a single global extremum is found when $$\frac{\partial R}{\partial \in}\bigg|_{\in = \in_{max}} = 0:$$

$$\in_{max} = \frac{\sum_n g'[n]f'[n]}{\sum_n f'[n]^2} \quad (8)$$

Due to the positivity of R and unchanging convexity of R with respect to $\in$, it is guaranteed that $\in_{max}$ minimizes R.

The two digital signals or channels are then combined through a channel selector or weighted sum to reduce signal discontinuities across different types of sensors (e.g., condenser microphones vs. piezoelectric sensors). Channel selection may be performed by a multiplexor between g[n] and Âf[n] based on the signal amplitude (e.g., switch at 90% of the lower gain channel), or through a weighted sum of the two channels dependent on the signal-to-noise ratio.

Figure 9A:
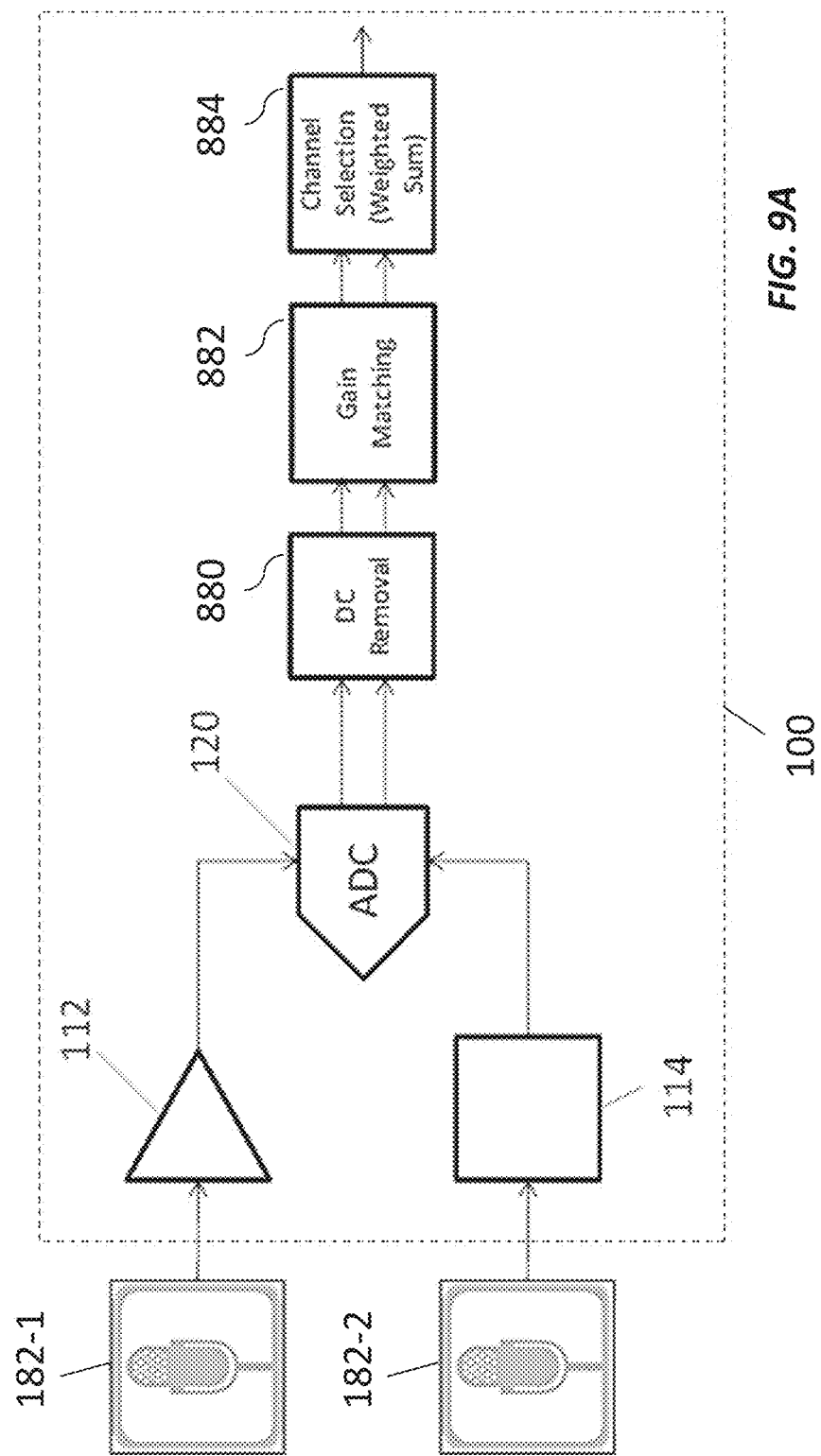
FIG. 9A is a block diagram illustrating a channel combination algorithm to extend dynamic range in accordance with some embodiments.

FIG. 9A is a block diagram illustrating how this algorithm for channel combination may be used with a stereo microphone system to extend dynamic range in accordance with some embodiments. In this case, the stereo microphone system includes at least two microphones 110-1 and 110-2 to convert audio-frequency vibrations into an analog electrical signals at different spatial positions. In some cases, the microphones may detect sound over different amplitude ranges. Microphone 110-1 is coupled in parallel to amplifier 112 to amplify the analog signal and effectively extend the lower edge of the system's amplitude range downwards. Microphone 110-2 is coupled in parallel to attenuator 114 to attenuate the analog signal and effectively extend the upper range of the system's amplitude range. The two signals are digitized separately by ADC 120, subjected to DC offset removal 880, subjected to gain matching 882, and finally combined through channel selection 884.

This algorithm for channel combination has been prototyped and tested. FIG. 9B is a series of plots illustrating an implementation of the full algorithm for an impulsive noise source, with an attenuation and gain channel on the same pressure sensor, in accordance with some embodiments. Plot 892 shows that the attenuation channel is selected during the high part of the impulsive noise source (158-162 ms). During a lower amplitude portion of the signal shown in plot 894, the gain channel is selected for its higher SNR. Note that the signals are well matched, even though they are put through two different amplification circuits. The gain matching and simple multiplexor used in this example demonstrates the effectiveness of this algorithm for channel stacking.

Additional On-Board Processing Improvements

In some embodiments, dosimeter signal processing is improved using an algorithm for removing false impulse signals by comparing data from an IMU/accelerometer against data from a microphone. The extraction and comparison of data originating from similar instances of impulses from the two components may help identify and remove false impulse signals in a noise recording. Analysis of signal frequencies and amplitudes, or general characteristics of the impulse (e.g., rise time, decay, ringing, etc.) may be used to differentiate a physical shock from a sound impulse and/or continuous noise.

In some embodiments, noise exposure estimates are improved using an algorithm for obtaining real-time barometric pressure by measuring barometric pressure, temperature, and humidity with at least one sensor and comparing the measurements with the environmental air pressure levels, as described above.

In some embodiments, noise exposure estimates are improved using an algorithm for real time SPL and event data logging via the use of GPS or another navigation system. By recording both impulses (and/or sustained continuous noise) and tagging the noise events with geo-temporal stamps, some embodiments may help create an event log ("breadcrumbs") documenting where multiple noise events have taken place over a period of time.

In some embodiments, noise exposure estimates are improved using an algorithm to calculate real time noise exposure using information from disparate sources, such as noise recordings, barometric pressure readings, and geo-temporal stamps.

Geo-Temporal Stamping of Impulse Noise

In some embodiments, a location of an impulse noise reading may be tagged using, for example, a satellite navigation device, such as a GPS receiver. The GPS receiver may be on board the dosimeter. In addition to tagging a location to an impulse noise event, a GPS receiver may be used to help characterize the impulse noise event by recording a time-stamp for the event. This may help to further characterize a noise exposure event by providing geo-temporal stamps in the truth data. In some embodiments, geo-temporal stamps may be collected from multiple disparate units (i.e., users) to localize a signal and/or reconstruct a signal profile in time and space by tracking of the sequence of multiple and/or related noise events.

Figure 10B:
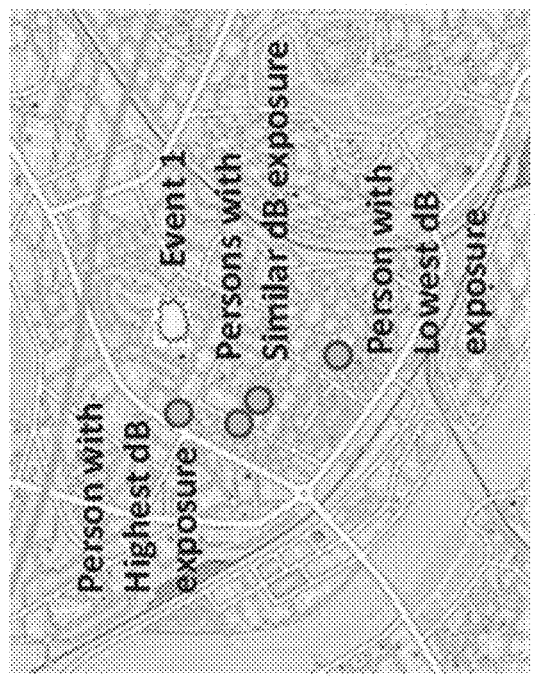
FIG. 10B is a display illustrating a map with symbols indicating a location corresponding to a noise exposure event based on positions of multiple users relative to the location in accordance with some embodiments.
Figure 10A:
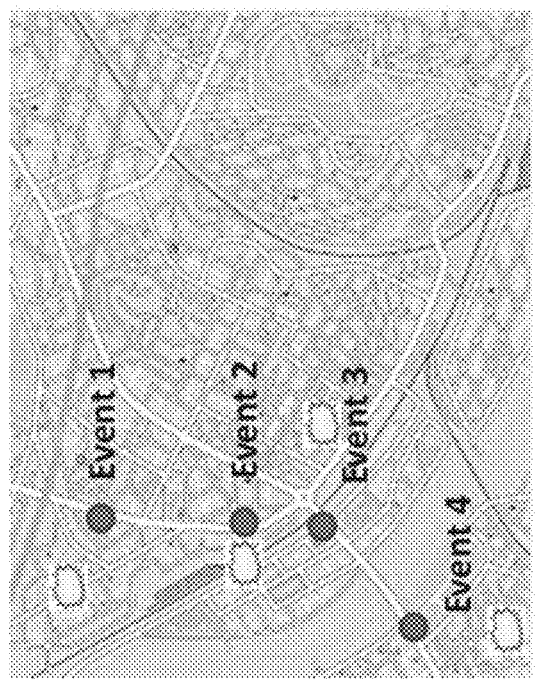
FIG. 10A is a display illustrating a map with symbols indicating locations corresponding to noise exposure events and a user position relative to those locations in accordance with some embodiments.

FIG. 10A is a display illustrating a map with symbols indicating locations corresponding to noise exposure events and a user position relative to those locations in accordance with some embodiments.

Networked Communications of Multiple Users in the Field

In some embodiments, network capabilities are provided. Information gathered and acquired from multiple users in a network may be synchronized and used to determine if one or more members or all the members in the network are overexposed. A networked capability in this capacity within the framework of the system may help to locate an impulsive noise event and can be of great benefit. If the relative position of each member is known when a noise event occurs, the geo-temporal stamps (with associated SPL level) can be shared through networking. If multiple individuals are exposed, any additional information may be used to locate or better locate the direction and possible distance of the noise source. The information also may be sent to, for example, a supervisor or squad/team leader to report or display (on, e.g., a cell phone) the status of individuals (e.g., at least one or each member of the squad/team).

FIG. 10B is a display illustrating a map with symbols indicating a location corresponding to a noise exposure event based on positions of multiple users relative to the location in accordance with some embodiments.

Behavioral Influence Via Feedback

In some embodiments, if a user is exposed to a predetermined number of high continuous or impulsive noise events or high continuous or impulsive noise for a predetermined period of time, feedback may be provided to the individual, for example, "Your daily threshold for noise exposure has been exceeded." The cumulative and compounding noise exposure can severely damage hearing, and hence this information may be used to influence the behavior of an individual (e.g., promote hearing protection and/or alter behavioral responses toward high levels of impulsive noise). The information also may be sent to, for example, a supervisor or squad/team leader to report or display (on, e.g., a cell phone) the status of individuals (e.g., at least one or each member of the squad/team).

Implantable and Array Embodiments

With the advances in microelectronics, such as systems on a chip (SOC), which are low size weight and power (SWaP) high capability devices, a dosimeter may be miniaturized for greater portability and even for implanting in a user. For example, micro-dosimeters deploying implantable surface or sub-dermal microphones may record noise events. If a miniaturized SOC has a built-in communication component, the recorded noise events may be processed and sent off via a radio communicatively coupled to the dosimeter. In some embodiments, micro-dosimeters may be implanted inside or near a user's ear for accurate ear canal-like noise measurements. In some embodiments, multiple micro-dosimeters may be implanted to form a ring or array of sensors around the head, such that the array of sensors records noise but also collects directionality of noise events. Augmenting this capability with other scalar information, such as geo-temporal stamps, the system may further enhance the recreation of the noise events.

FIG. 11 is a diagram illustrating a micro-dosimeter to be attached to or implanted in a subject (e.g., near or inside each of a subject's ears) in accordance with some embodiments.

Self-Calibration for Individual Users

In some embodiments, a system includes a calibration tone that is played periodically into the microphones for routine calibration of frequency and amplitude responses of the microphones. As such, the hardware response to a certain noise (dB) level may be maintained and calibrated to ensure that the microphones are working properly at all times. In some embodiments, the system also includes a pressure chamber (with a predefined pressure level) around the altimeter to periodically determine and/or monitor the altimeter response to a known pressure level. The pressure chamber then may be open to the environment during normal operation and, while not in active use, it may be closed and/or pressurized for self-calibration.

Examples

Noise exposure and the subsequent hearing loss are well documented aspects of military life. Numerous studies have indicated high rates of NIHL in active-duty service men and women, and recent statistics from the U.S. Department of Veterans Affairs indicate a population of veterans with hearing loss that is growing at an increasing rate. In an effort to minimize hearing loss, the U.S. Department of Defense (DoD) updated its Hearing Conservation Program in 2010, and also has recently revised the DoD Design Criteria Standard Noise Limits (MIL-STD-1474E), which defines allowable noise levels in the design of all military acquisitions including weapons and vehicles. Even with such mandates, it remains a challenge to accurately quantify the noise exposure experienced by an individual over the course of a mission or training exercise, or even in a standard work day. Noise dosimeters are intended for exactly this purpose, but variations in device placement (e.g., free-field, on-body, in/near-ear), hardware (e.g., microphone, analog-to-digital converter), measurement time (e.g., work day, 24-hour), and dose metric calculations (e.g., time-weighted energy, peak levels, Auditory Risk Units), as well as noise types (e.g., continuous, intermittent, impulsive) can cause exposure measurements to be incomplete, inaccurate, or inappropriate for a given situation.

Some embodiments are directed to predictive modeling of, recording, and/or processing sound pressure in an environment subject to both continuous noise and impulse noise, both of which may contribute to NIHL. According to some embodiments, a noise dosimeter capable of acquiring exposure data across tactical environments is disclosed. To help fill the gap in dosimetry technology appropriate for the military, Massachusetts Institute of Technology Lincoln Laboratory (MIT LL) is developing a noise dosimeter with the goals of capturing noise exposure for individuals through on-body sensors and providing acoustic characterization of both continuous and impulsive sounds.

Two generations of prototypes have been constructed and tested. The first-generation prototype device was fielded in 2013 with dismounted Marines in Afghanistan by the Marine Expeditionary Rifle Squad (MERS) as part of a joint protocol with the U.S. Army Research Institute of Environmental Medicine (USARIEM). The second generation prototype is a laboratory-grade, portable dosimeter that is funded jointly by MERS and the U.S. Army Natick Soldier Research, Development, and Engineering Center (NSRDEC). In accordance with some embodiments, the second-generation device will meet nearly all the instrumentation standards for impulse noise outlined in MIL-STD-1474E and provide additional functionality and sensors, such as accelerometers to help filter out false noise events from objects hitting the microphones. Further details about the prototypes are provided below.

Utilizing embodiments for on-body measurements and collecting coordinated audiometric tests on individuals during military operations may generate important data sets for evaluating existing noise metrics and validating new ones. Opportunistic data collections of this type during military operations may reduce reliance on the unique Albuquerque blast overpressure walk up study (Johnson, 1993) and may help to inform individual susceptibility for NIHL by including other physiological and genetic factors.

Figure 12:
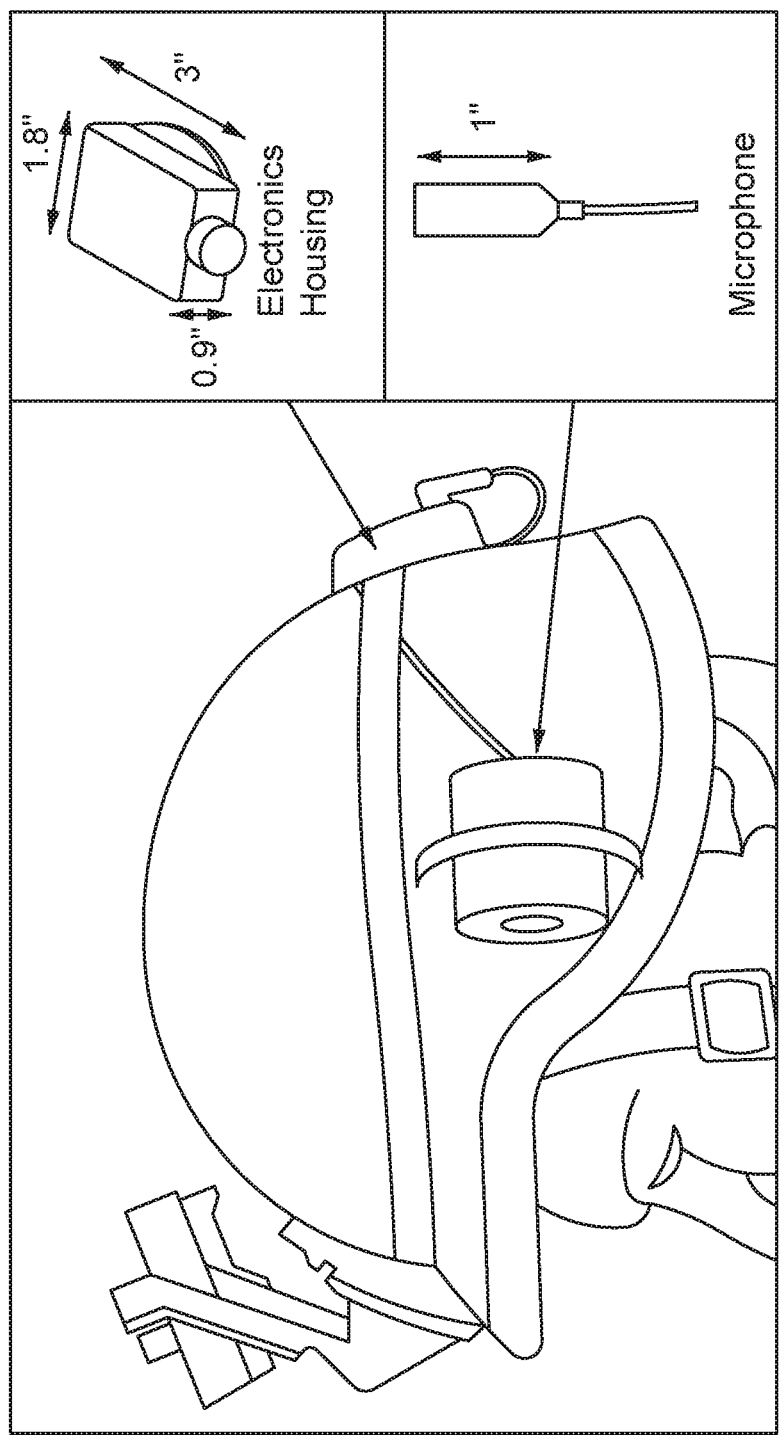
FIG. 12 is an image illustrating a first-generation prototype dosimeter system in accordance with some embodiments.

FIG. 12 is an image illustrating the first-generation prototype in accordance with some embodiments. In FIG. 12, the compact, portable system 100 and stereo microphone system 110 of FIG. 2C are mounted on the back of a helmet 200 for collecting audio data in a rugged environment (e.g., a battlefield). Stereo microphones 110-1 and 110-2 (not shown) are mounted on the left and right sides of the helmet, close to the ears of the person wearing the helmet 200. Because the microphones are mounted near the person's ears instead of elsewhere, they capture audio data that more accurately represents what the person actually hears while wearing the helmet 200.

System 100 may be used to record ambient sounds with a peak amplitude of about 180 dB at a bandwidth of about 50 kHz. In one case, the system's amplitude range extends from about 81 dB to about 173 dB, for a total dynamic range of about 92 dB, with the stereo channels from each microphone spanning about 58 dB each. The recorded digital data preserves the spectral characteristics of the ambient sounds and captures the rise time and spacing of impulsive sounds (e.g., gunshots and explosions) within earshot of the person wearing the helmet 200.

Depending on the battery life, memory size, and device temperature, the system 100 may record for up to 24 hours without imposing any unacceptable risks (e.g., of battery explosion) on the person wearing the helmet 200 or others near the helmet 200. For instance, the battery life and memory size may be long enough and large enough, respectively, to support eight hours or more of continuous 16-bit recording at a bandwidth of about 32 kHz. If desired, system 100 may be reprogrammed or switched among operating modes to extend the collection period. In one mode, system 100 may act as a noise dosimeter that records only the peak audio levels integrated across some or all of the audio band; in another mode, system 100 may record high-resolution audio data.

As shown in FIG. 12, system 100 may be mounted in a housing 190 with a small, robust form factor. In the example shown in FIG. 12, the housing 190 has exterior dimensions of about 80 mm×55 mm×10 mm and is made of injection-molded plastic, resin, or any other suitable material. The housing 190 includes outer halves 192 and 194 that fit together to form an enclosed cavity, which holds a circuit board 152 with the electronic components (ADC 120, processor 130, etc.) shown in FIGS. 1A-1D and a battery 154, such as an NiMH or NiCad rechargeable battery, that powers the circuit board 152. Audio jacks 198 fit into apertures in the housing 190 and connect the components on the circuit board 152 to the microphones. When fully assembled, system 100 (including the housing 190) weighs about 40 g or less, including the microphones.

A magnetic screw 196 or other actuator, such as a switch, may be used to turn the system 100 on or off. For example, tightening the magnetic screw 196 moves the magnet 196 in closer to a Hall effect sensor (not shown), which produces an output whose voltage changes in response to the increase in magnetic field strength. The processor, which is coupled to the Hall effect sensor, detects this change in voltage and starts the recording process. Loosening the magnetic screw 196 reduces the magnetic field sensed the by the Hall effect sensor, which produces another voltage change that causes the processor to stop recording audio data.

A wearable, high sampling rate, broad spectrum noise dosimeter attached to a helmet may include at least two microphones co-located, for example, with an accelerometer to detect false impulse signals. According to some embodiments, the system is capable of self-calibration and provides real-time processing of data including voice removal, peak amplitude, kurtosis, max dB level, average dB level, and/or noise exposure (e.g., dosage) and reporting of noise exposure as it pertains to several existing (or future models) such as the AHAAH.

Those of skill in art will readily appreciate that an audio recording system could also be mounted in a housing with a different size, shape, and/or weight. The housing could also be made of a different material (e.g., stamped pieces of metal) or omitted altogether. For instance, the system components could be stitched into or onto an article of clothing, such as a jacket or shirt, or into or onto a bag, web gear, or any other suitable article with or without the microphones. The system could also be mounted on or in a portable device, vehicle (e.g., inside an aircraft cabin, racecar, construction vehicle, etc.), or in a particular location (e.g., a shop floor). One or more system components may be wearable and/or implantable.

Figure 13:
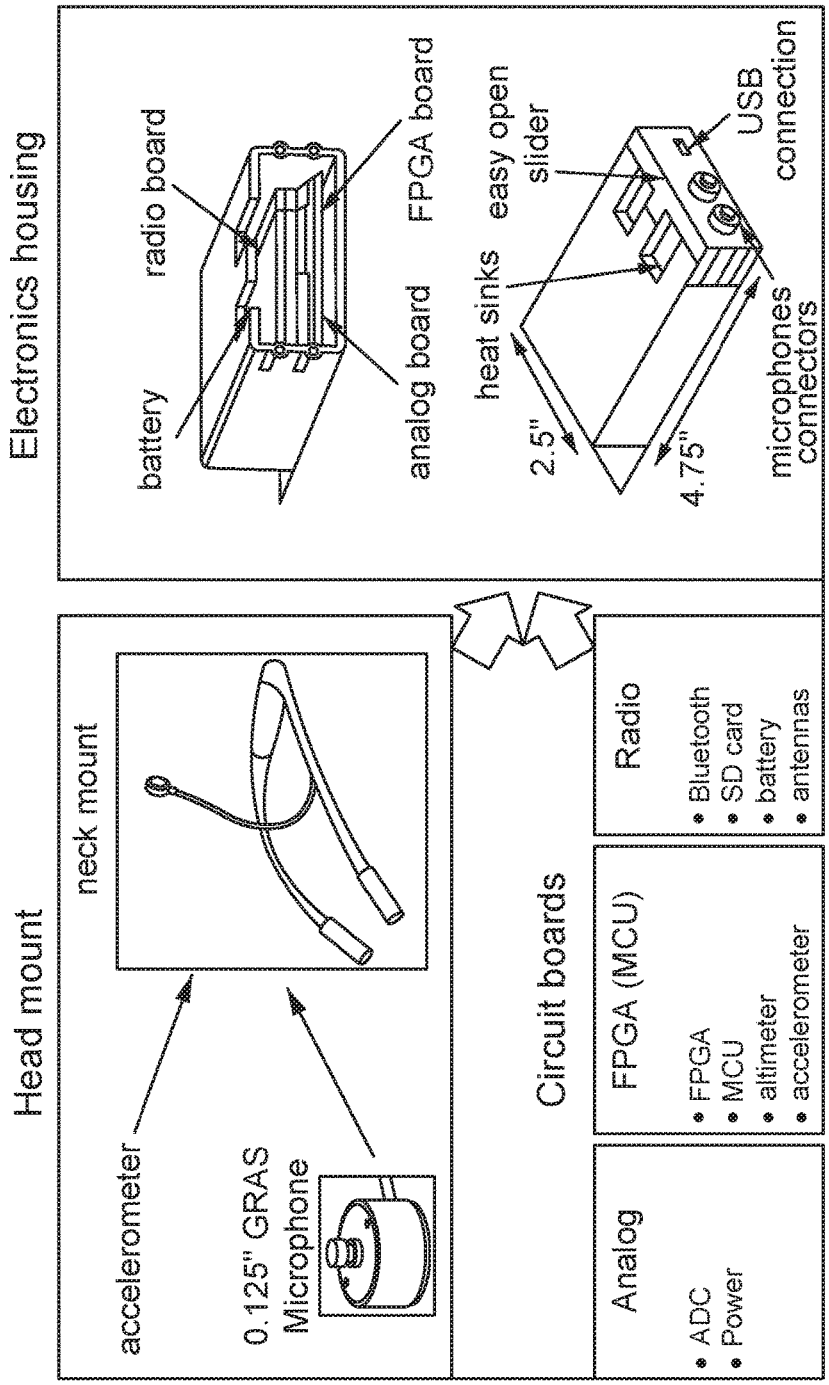
FIG. 13 is a diagram illustrating a dosimeter system in accordance with some embodiments.

FIG. 13 is a diagram illustrating a high fidelity noise exposure recording system in accordance with some embodiments. The recording system may be designed for mounting on a user's head, attaching to, for example, the neck, ear, etc. The recording system includes a microphone (e.g., a 0.125-inch microphone) and an accelerometer. The recording system includes at least one circuit board, such as an analog board for regulating power and/or A/D conversion; an FPGA/MCU board for controlling onboard processing, altimeter measurements, GPS communications, temperature sensing, humidity measurements, and/or IMU measurement; and a radio board for controlling at least one communication interface (e.g., Bluetooth®, antenna, etc.), a data storage device, and/or a power source (e.g., a battery or rechargeable battery). Together, the power source and the at least one circuit board may be situated in an electronics housing featuring heat sinks, an access opening (e.g., an easily slidable opening), microphone connectors, and/or USB connections.

Although Bluetooth® communication is widely used in the commercial sector for communication due to its ease of use and range, this method is unacceptable in a tactical environment because it is easy to detect. In some embodiments, a dosimeter has the capability to use either a Bluetooth® radio or to include a wideband or narrowband tunable radio onboard with a defined power level and range. The latter radio allows the system to communicate data in a tactical, and potentially covert, manner. The integrated radio (e.g., Bluetooth® or tunable narrow band) may be used to link several systems to form a real-time network.

Figure 14:
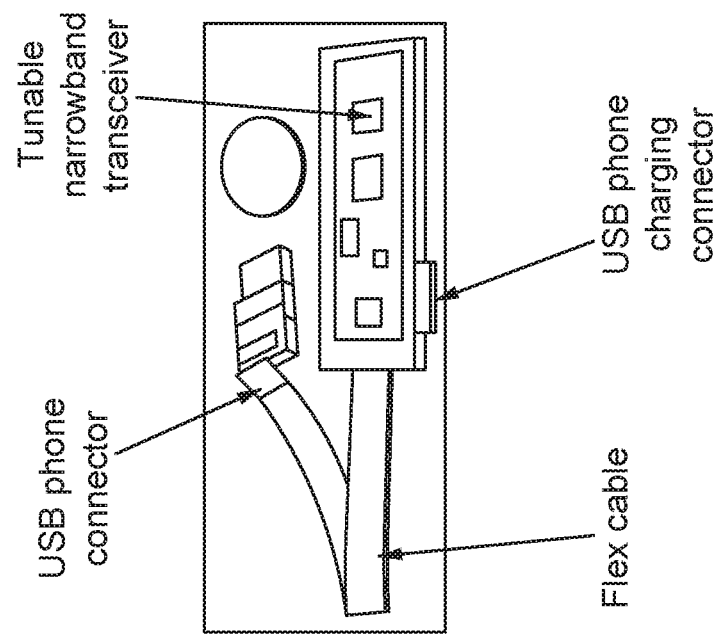
FIG. 14 is a diagram illustrating dosimeter system components in accordance with some embodiments.

FIG. 14 is a diagram illustrating dosimeter components including a USB connector to connect with, for example, a phone (e.g., a smartphone) in accordance with some embodiments. The USB may be connected to the phone via a (e.g., flexible) cable. The dosimeter components in FIG. 14 also include a tunable wideband or narrowband radio onboard with a defined power level and range to communicate data in a tactical, and potentially covert, manner in accordance with some embodiments.

The second-generation noise dosimeter was aimed at improving the signal quality above that of the original version, through modifications to both the internal circuitry and the microphones (left and right). The goal for this device was to collect on-body, laboratory-grade measurements that meet or are close to instrumentation requirements specified in MIL-STD-1474E, while maintaining a suitable form factor. In addition, several auxiliary sensors are integrated into the device to capture GPS data, temperature, barometric pressure, and acceleration. The accelerometer is particularly valuable for its ability to identify physical impacts that produce false impulse-like signals on the microphone.

Figure 15:
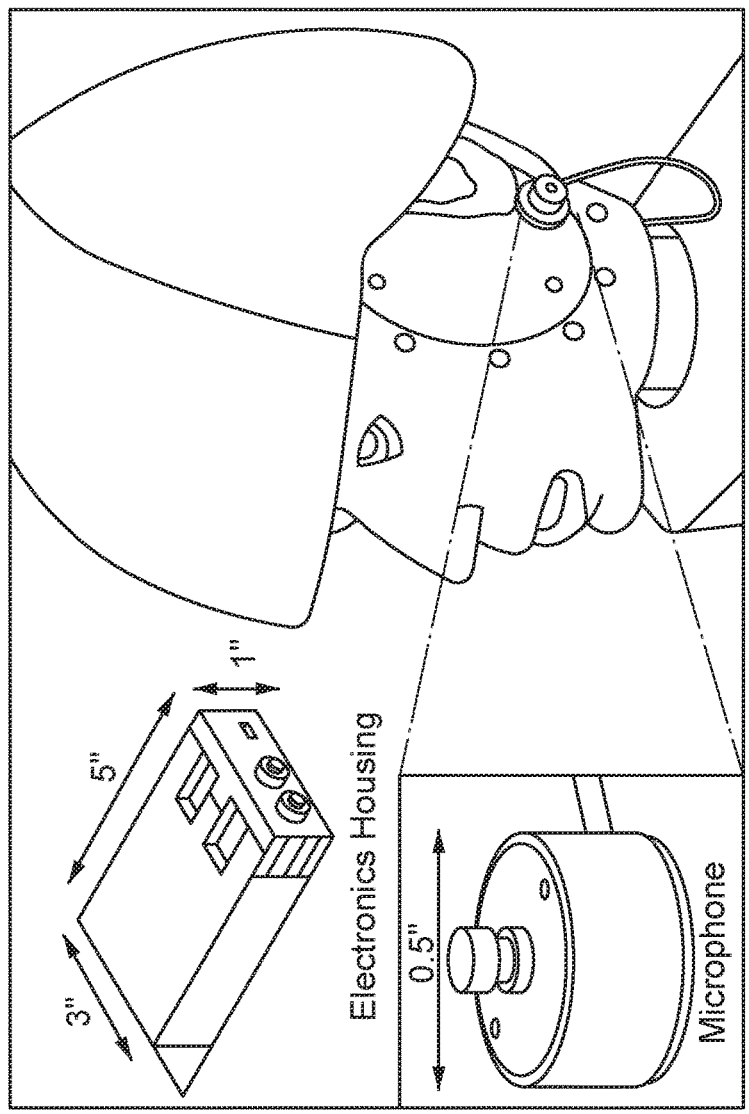
FIG. 15 is an image illustrating a second-generation prototype dosimeter system in accordance with some embodiments.

FIG. 15 is an image illustrating the second-generation prototype in accordance with some embodiments. A GRAS 47DX ⅛" pressure microphone was selected for the microphone in the second-generation dosimeter design due to its form factor (suitable for near-ear placement), its large measurement range (up to 185 dB), and its frequency response (up to 100 kHz). Although ideal for research studies, one downside to this microphone is the cost, which might prevent wide-scale adoption for occupational and military noise measurements. However, some embodiments may be built with less costly microphones that have sufficient signal bandwidth and quality. In some embodiments, the product size may be reduced while battery life is increased to enable extended periods of use (e.g., weeks to months). For example, the sample rate has a strong effect on the power consumed by the analog-to-digital converter, but also on any processing that must be done on the resulting digital data. The analog-to-digital converter used in the device, which has 128 kHz sampling frequency and a 285 mW power consumption, was selected for being a midpoint in the trade-off between SWaP and data quality.

Figure 16:
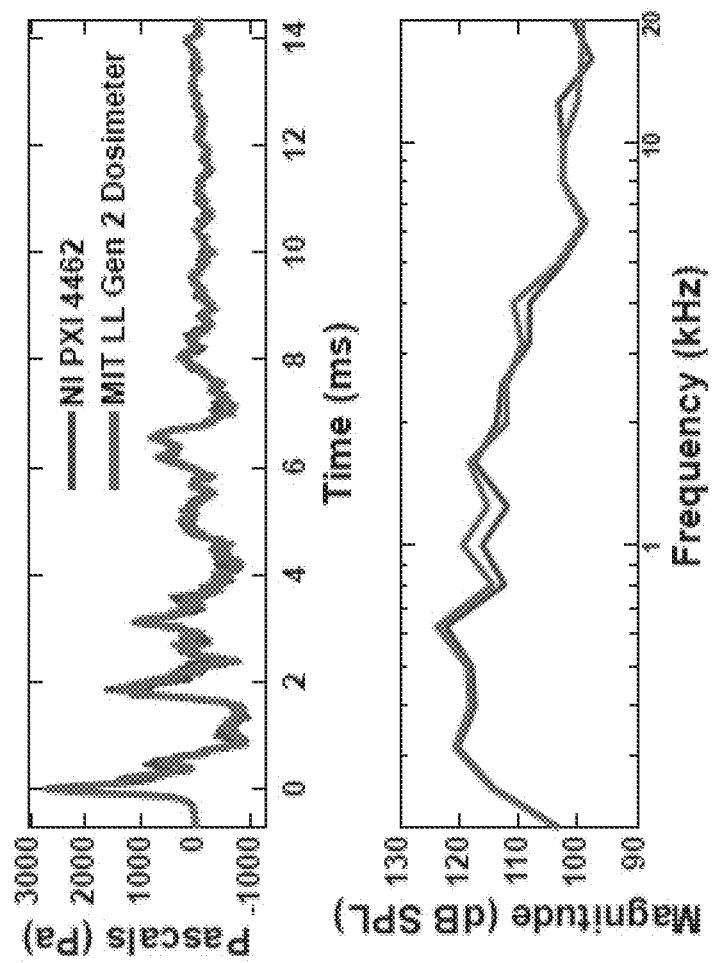
FIG. 16 is a series of plots illustrating pressure waveforms and ⅓-octave-band spectra collected with the second-generation prototype dosimeter system in accordance with some embodiments.

To verify the accuracy of the MIT LL second-generation dosimeter, simultaneous laboratory measurements were made with the dosimeter and a reference data-acquisition system using two GRAS 47DX microphones co-located near the ear of an acoustic test fixture. FIG. 16 is a series of plots illustrating pressure waveforms (top) and ⅓-octave-band spectra (bottom) for the MIT LL 2nd-generation noise dosimeter and a reference data-acquisition system collected with matching, co-located microphones in accordance with some embodiments. There is a good correspondence between the two systems. FIG. 16 contains an example of the data collected for a 161-dB peak SPL impulse noise generated from a compressed-air shock tube. The second generation dosimeter shows good correspondence to the reference system, a 24-bit National Instruments laboratory-grade system that samples at 200 kHz. The dosimeter measured a peak SPL of 161.0 dB and an $L_{Aeq,100ms}$ of 136.7 dB, while the reference system measured a peak SPL of 161.3 dB and an $L_{Aeq,100ms}$ of 137.2 dB. The median difference in the ⅓-octave-band levels was 0.7 dB.

Another important consideration in the dosimeter design is the choice of damage risk metrics to be output by the device, ideally computed in real-time. Since the second-generation prototype is designed for research and the damage risk metrics have not yet been settled on, the prototype is typically configured as a sound recorder and evaluation of noise exposure metrics is performed off-line. The prototypes are, however, capable of on-board data processing via a Xylinx Zynq, which includes both an FPGA and dual-core ARM processor. A hybrid approach for storage of continuous and impulse noise may be used to reduce the data storage requirements (e.g., about 3 GB per hour for stereo recording) on the tactical noise dosimeter while preserving select time-pressure intervals for further analysis. In this hybrid approach, data are stored in two output streams on different time-scales. Average A-weighted levels or octave bands of the background noise levels are captured on a relatively slow, uniformly sampled time scale. Simultaneously, impulses that exceed a threshold are detected and stored as full pressure waveforms for offline analysis since impulse metrics are less agreed upon by the hearing community. This technique reduces the data storage requirements while still capturing significantly more information than a COTS noise dosimeter. Currently, the prototype dosimeter has 128 GB of available storage through a microSD card.

Figure 17:
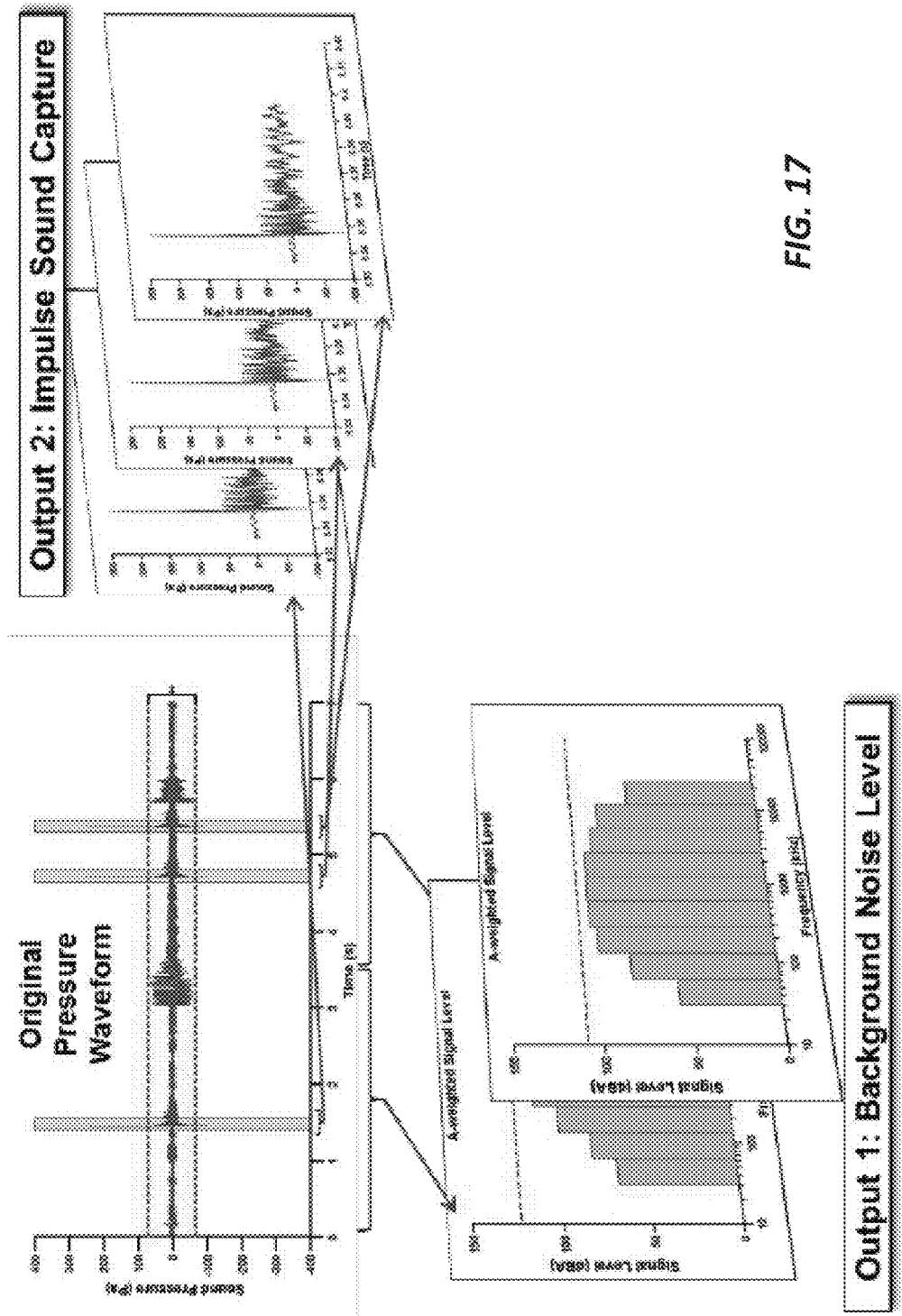
FIG. 17 is a diagram illustrating a signal processing and data storage algorithm for a complex-noise, tactical noise dosimeter in accordance with some embodiments.

FIG. 17 is a diagram illustrating a signal processing and data storage algorithm for a complex-noise, tactical noise dosimeter in accordance with some embodiments. Output 1 consists of background noise level measurements (e.g. sound level or octave band measurements at 1 s intervals). Output 2 consists of the full pressure waveform when an impulse noise event is detected. This technique allows for application of existing and future damage risk metrics to be applied specifically for impulse noise, while reducing the data storage requirements, in accordance with some embodiments.

Lessons learned from field collections with COTS recorders and the first-generation dosimeter also have helped inform the design of the second generation dosimeter package. The interface of the device has no settings that are exposed in order to limit opportunities for human error. A display to indicate the status of the device (verify functionality and system health) will be added for identifying device concerns during a fielding. Another challenge with on-body dosimetry is artifacts due to acceleration effects or touching the microphone. Knocking artifacts recorded in an acoustic waveform are very similar to impulsive noise, but since they are not representative of the noise transmitted to the ear drum, they can result in gross over-estimates of the noise exposure if they are integrated into personal dose estimates. In the Afghanistan fielding of helmet-mounted noise dosimeters, dropped helmets and other impacts associated with military operations produced a large number of artifacts in the data that could not be automatically screened from the dosage calculations. Microphone design and diaphragm size can have a strong effect on acceleration sensitivity, which is typically maximal in the direction of diaphragm motion. Hearing aid and MEMS microphones typically have low acceleration sensitivity and are ideal for on-body acoustical recording, but do not span the dynamic range for military noise exposures. Piezoelectric microphones may also be a good option, but are often less sensitive in the range of human acoustic sensitivity. The MIT LL second-generation dosimeter has been designed with co-located accelerometers at each microphone and in the device enclosure. These additional sensors will be used to help detect and remove microphone knocking through on-board processing described above in accordance with some embodiments.

In 2013, several Marines in Afghanistan were outfitted with the MIT LL first-generation on-body dosimeters in a study conducted by MERS and USARIEM Noise exposure was measured for approximately 12 hours each day over a period of two days, providing samples of the operational noise environment. Participants received a briefing on the study and were outfitted with either an MIT LL helmet sensor or a COTS TASCAM DR-05 recorder. Ten of each device were available for the fielding. On each day, two platoons completed their daily patrol with the devices recording. The Marines transitioned between being mounted in vehicles and walking in the vicinity while on patrol. None of the Marines wore hearing protection.

Figure 18:
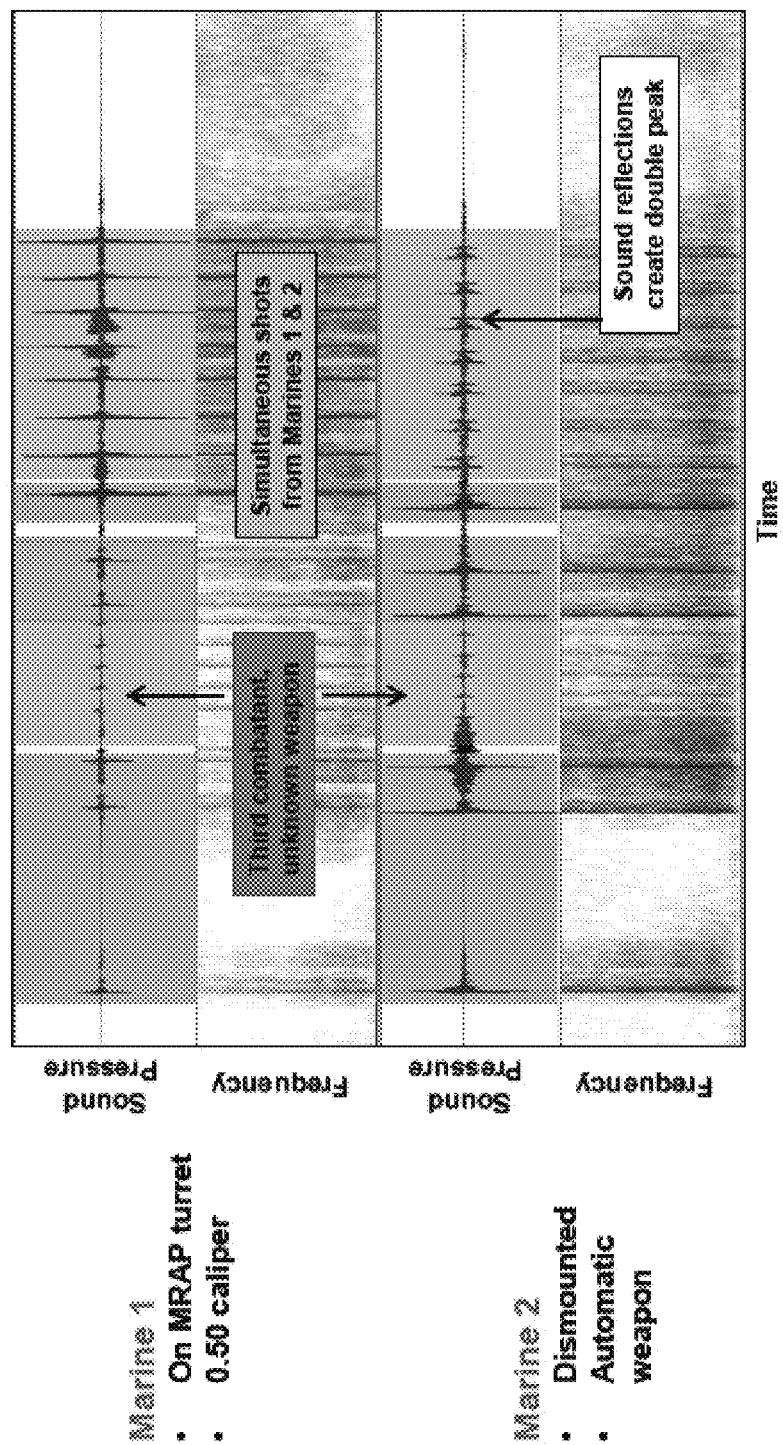
FIG. 18 is a series of simultaneous recordings illustrating live weapons fire as observed by two individuals fielding on-body dosimeters in accordance with some embodiments.

FIG. 18 is a series of simultaneous recordings of live weapons fire as observed by two Marines with on-body dosimeters in accordance with some embodiments. In FIG. 18, the data was recorded by the sensors for two Marines in close proximity to each other during a firefight. Three different combatants can be heard firing in the recording, where the exposure for Marine 1 is highest during the last section, and in the first section for Marine 2. These data demonstrate the complicated noise dosage that accumulates based on the position relative to the impulse noise source, and thus the need for on-body sensors to make personalized measurements.

Damage risk metrics such as those listed in TABLE 1 have been calculated from the recorded data. One challenge that arose in evaluating the dose from the Afghanistan collection is that knocking artifacts frequently occurred from the motion of the Marines and incidental contact with the microphones. Under these circumstances, directly integrating the A-weighted energy over the full 12 h recordings would result in inflated dose values since much of the energy comes from the knocking artifacts. To avoid this, a number of artifact-free intervals were manually identified and analyzed. TABLE 3 shows the damage risk metrics for the short interval shown in FIG. 18.

TABLE 3

| Location | Analysis Interval | Impulse Count | Peak SPL (dB) | $L_{Aeq, 8h}$ (dBA) | $L'_{Aeq, 8h}$ w/ Kurtosis dBA) | $L_{IAeq, 8h}$ (dBA) | AHAAH Unwarned (ARU) | AHAAH Warned (ARU) |
|---|---|---|---|---|---|---|---|---|
| | | | | | Criterion | | | |
| | | | ≤140 | ≤85 | ≤85 | ≤85 | ≤200/500 | ≤200/500 |
| Afghanistan: Marine 1 | 6 sec | 19 | 152 | 85 | 92 | 76 | 2699 | 463 |
| Afghanistan: Marine 2 | 6 sec | 19 | 150 | 84 | 91 | 78 | 1596 | 140 |

TABLE 3-continued

| Location | Analysis Interval | Impulse Count | Peak SPL (dB) ≤140 | $L_{Aeq, 8h}$ (dBA) ≤85 | $L'_{Aeq, 8h}$ w/ Kurtosis dBA) ≤85 | $L_{IAeq, 8h}$ (dBA) Criterion ≤85 | AHAAH Unwarned (ARU) ≤200/500 | AHAAH Warned (ARU) ≤200/500 |
|---|---|---|---|---|---|---|---|---|
| Carrier: Room 1 | 24 h | 0 | 123 | 75 | 76 | n/a | n/a | n/a |
| Carrier: Room 2 | 24 h | 0 | 122 | 79 | 81 | n/a | n/a | n/a |
| Carrier: Room 3 | 24 h | 24 | 143 | 81 | 84 | 58 | 1800 | 695 |

During this short 6 second interval, both Marines are exposed to equivalent noise levels $L_{Aeq,8h}$ near the recommended daily limit of 85 dBA. Peak levels observed from the shots fired nearest to them exceed the recommended limit of 140 dB. The MIL-STD-1474E impulse metrics, $L_{I\ Aeq,8h}$ and AHAAH ARU, are only calculated on the impulses and exclude background energy. The corrected $L_{I\ Aeq,8h}$ metric yields a value several dB lower than the conventional $L_{Aeq,8h}$. Although the impulses in this data were due to small arms fire, the A-duration estimation resulted in correction factors that reduced the energy of each impulse by several dB (ranging from 4 to 16.5 dB for the 19 shots shown). The last metrics shown in the table are AHAAH ARU calculated for the Unwarned (middle ear reflex not active prior to the arrival of each impulse) and Warned (middle ear reflex active prior to the arrival of each impulse) states. In the Unwarned state, the 500 ARU limit for occasional exposure is significantly exceeded. However, assuming the ear is in the Warned state, which may be a reasonable assumption for a soldier firing his or her own weapon, the ARU falls slightly below the limit.

Other prominent noise sources in military environments include ground, air, and sea-based vehicles. In particular, aircraft carriers are among the loudest of military environments; above deck, personnel wear double hearing protection to protect against the extreme noise levels from jets as they launch and land on the carrier. However, the noise levels are high even below deck, with a complex mix of continuous, intermittent, and impulsive noise events from many contributing sources.

Figure 19:
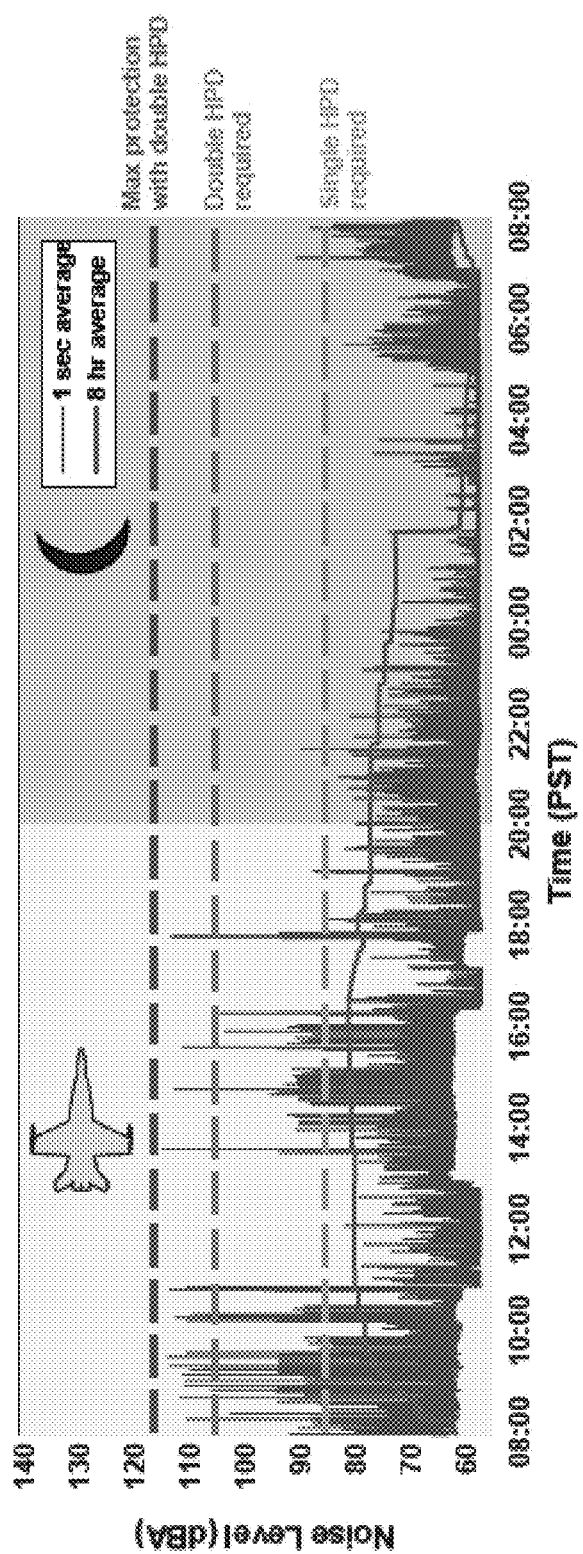
FIG. 19 is a plot illustrating 24-hour dosimeter collection on an aircraft carrier in accordance with some embodiments.

FIG. 19 is a plot illustrating an example of the 24-hour dosimeter collection on an aircraft carrier showing high intermittent/impulsive noise in a living space at the front of the ship during flight operations and lower (but still moderately high) levels after flight operations conclude in accordance with some embodiments. The data was collected in a study funded by the Office of Naval Research (ONR) in collaboration with Noise Control Engineering LLC during a Joint Strike Fighter (JSF) exercise. Noise was recorded throughout the seven-day exercise using stationary, free-field COTS sensors (TASCAM DR-40 recorders). Significant background levels were observed in the living spaces below deck, and persistent recordings show shifts in the continuous background levels that range from 55 dBA (the noise floor of the recorder) up to 62 dBA. The elevated background levels correspond to time periods leading up to flight operations and likely are associated with high loads on support machinery in use. Prior to launch, the fighter jets engage engines at full power, producing intermittent bursts of high-intensity noise that last for 20 to 30 seconds. Finally, occasional impulses are observed in the data, associated with the catapult brake that produces a sharp impact noise that reverberates through the ship as each aircraft is launched.

TWA noise levels are represented in FIG. 19 as an 8-hour moving average of the noise measurements (solid red line). The average level in this living space during flight operations is just above 80 dB. For comparison, the Navy guidance for 8-hour TWA noise levels where single and double hearing protection devices (HPDs) are required are shown as dashed lines. The upper-most dashed line represents the noise reduction rating for the best double HPD approved by the DoD.

This 24-hour measurement shows that noise in the living quarters below deck of an aircraft carrier reaches very high levels during flight operations and the noise continues at moderately high levels even after flight operations conclude. These 24/7 noise conditions may not support full TTS recovery each day. Further on-body and in-ear dosimeter measurements along with audiometric data are needed to better understand this issue, as the accumulated risk of hearing damage might be significantly greater when exposures from the flight-deck are included.

Figure 20:
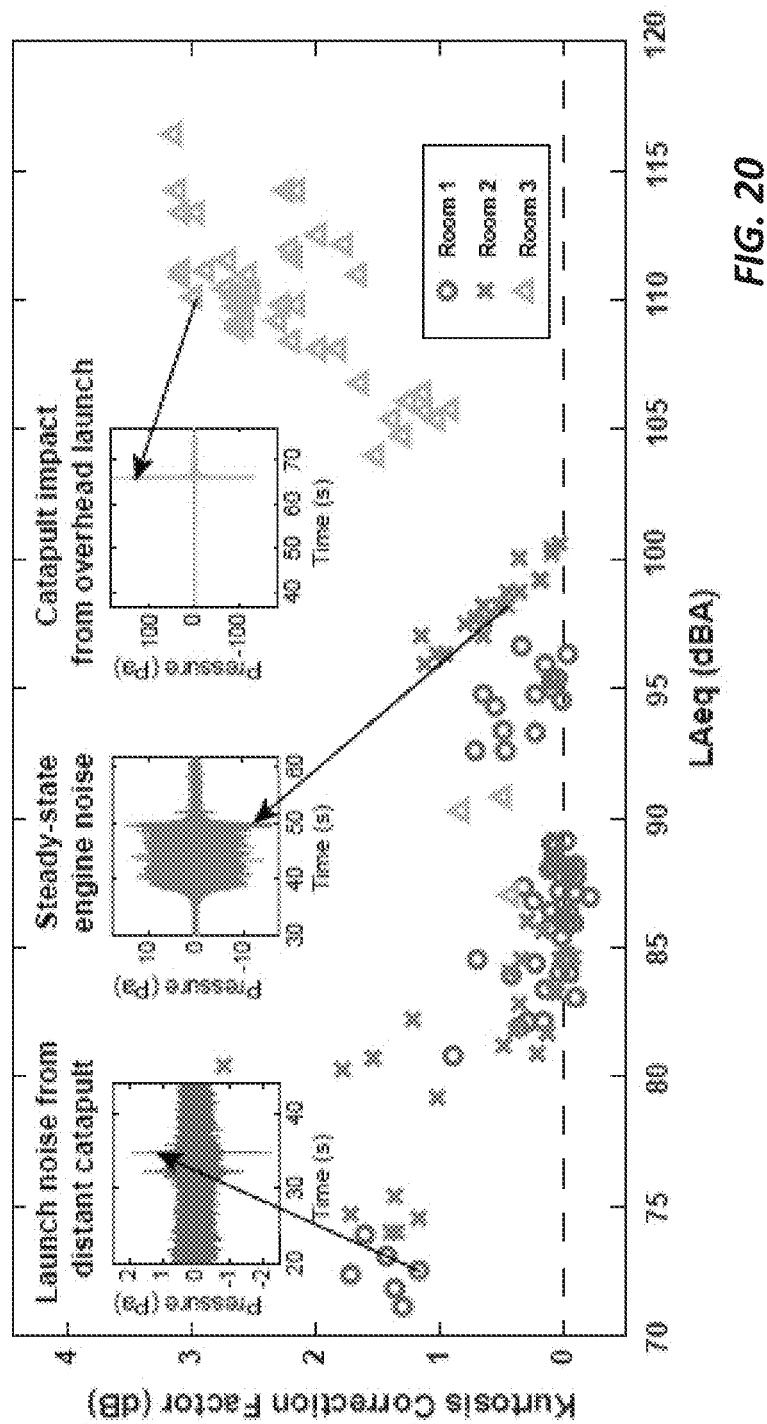
FIG. 20 is a scatter plot illustrating damage risk metrics calculated from the 24-hour dosimeter collection on the aircraft carrier in accordance with some embodiments.

FIG. 20 is a scatter plot of example damage risk metrics calculated from the noise recordings in living spaces below deck in accordance with some embodiments. Each point represents the A-weighted noise level for each launch plotted against the corresponding kurtosis correction based on the approach described by Goley et al. (2011), calculated during a 1 second interval of an aircraft launch from the catapult overhead. Rooms 1 and 2 are located below the jet blast deflectors, so the primary noise exposure is from intermittent, continuous-noise jet engine blasts. Furthermore, the launch energy is not highly impulsive, so the kurtosis-correction factor is generally small in these rooms. Room 3, located at the front of the ship in close proximity to the breaking mechanism for the catapults, contains the loudest noise during launches, as indicated by the higher $L_{Aeq,8h}$ values. Additionally, the noise in this room is highly impulsive, as seen in the example waveform in the inset of FIG. 20, leading to relatively large kurtosis-based correction factors for most of the launches in this room.

TABLE 3 also summarizes the metrics for the three aircraft carrier rooms accumulated over a 24 h period where 22 aircraft were launched from the catapults overhead. Since Rooms 1 and 2 did not contain high-level impulses, the impulse metrics $L_{Aeq,8h}$ and AHAAH ARU are not appropriate metrics for these rooms, but the $L_{Aeq,8h}$ characterizes the continuous and intermittent noise energy accumulated throughout the day. The $L_{Aeq,8h}$ is below the recommended 85 dBA limit, but considering that they are living spaces, the 75-79 dB levels may not provide adequate recovery conditions for personnel during their off-duty hours. Applying a kurtosis correction increases the equivalent noise levels by 1-2 dB. In Room 3 the impulse peak levels are much higher, reaching the 140 dB peak limit for most launches. For this room the impulse metrics $L_{Aeq,8h}$ and AHAAH ARU are calculated for high-level peaks as well as the conventional $L_{Aeq,8h}$ integrated over the full 24 hour period. The damage risk metrics give conflicting results: both the conventional and kurtosis-corrected $L_{Aeq,8h}$ are close to, but below the recommended 85 dBA limit. The impulse metric $L_{Aeq,8h}$ which integrates over the 100 ms window for each impulse (neglecting all intermittent and continuous background noise) yields a very low hazard. The value is particularly low because A-duration calculations are not well-suited for the highly-reverberant impact noise observed in this room. Due to the reverberation, A-durations calculated for these impulses are typically longer than 2.5 ms, resulting in the maximum reduction of 16.5 dB in the $L_{Aeq,8h}$ risk metric. Conversely, the AHAAH ARU metric predicts extreme hazard from the impulses in this room for both Warned and Unwarned states. The inconsistencies seen between $L_{Aeq,8h}$, $L_{I\ Aeq,8h}$, and AHAAH ARU damage risk metrics for this room, as well as the uncertainty in when to consider Warned versus Unwarned AHAAH ARU in this noise environment, emphasize the need for further research to understand the limitations of damage metrics and develop clearer guidelines for which metric or metrics should be used in a scenario.

With decades of investment in noise assessments, the military has extensive recordings from stationary measurement systems collected on ships, ground vehicles, aircraft and other relevant noise environments. In a diffuse, continuous sound field it is possible to leverage existing measurements or acoustic models of a noise environment such as a Navy ship and generate representative free-field noise metrics for a specific room or location. While these free-field noise metrics provide valuable information about noise conditions throughout the ship, they fall short of estimating the individual exposure of a crew member, since personnel move throughout the ship over the course of a day and the exposure of an individual is unique based on his or her sequence of activities. Estimating a dose for a given individual relies on layers of assumptions about personnel movement above and below deck over a 24 hour period as well as when crew are wearing hearing protection devices (HPDs). Similarly, while noise level recordings of individual weapons or vehicles are readily available, there are no noise exposure collections during dismounted combat operations.

Uncertainties associated with estimating personnel movement as they perform their duties may be avoided with on-body dosimetry where the local noise conditions are directly sampled by the device in accordance with some embodiments. On-body measurements may also be valuable for the purpose of developing task-based transfer functions which could be used to translate extensive collections of free-field military environment measurements into representative dosage for a given task.

Another level of fidelity needed to capture the dose experienced by an individual is to relate the noise measured at a position on the body to the noise arriving in the ear canal. This requires a transfer function to account for spatial, spectral, and temporal filtering of the noise by the torso, head and outer ear. While the top of the shoulder is historically considered an optimal position for a dosimeter microphone, the differences in sound pressure among on-body locations can vary up to 15 dB, which could impact temporary and permanent threshold shifts significantly. This problem is even more relevant for military and impulse noise, where head and helmet shadowing and pinna resonances can strongly effect the high-frequency content of the energy delivered to the eardrum.

Figure 21:
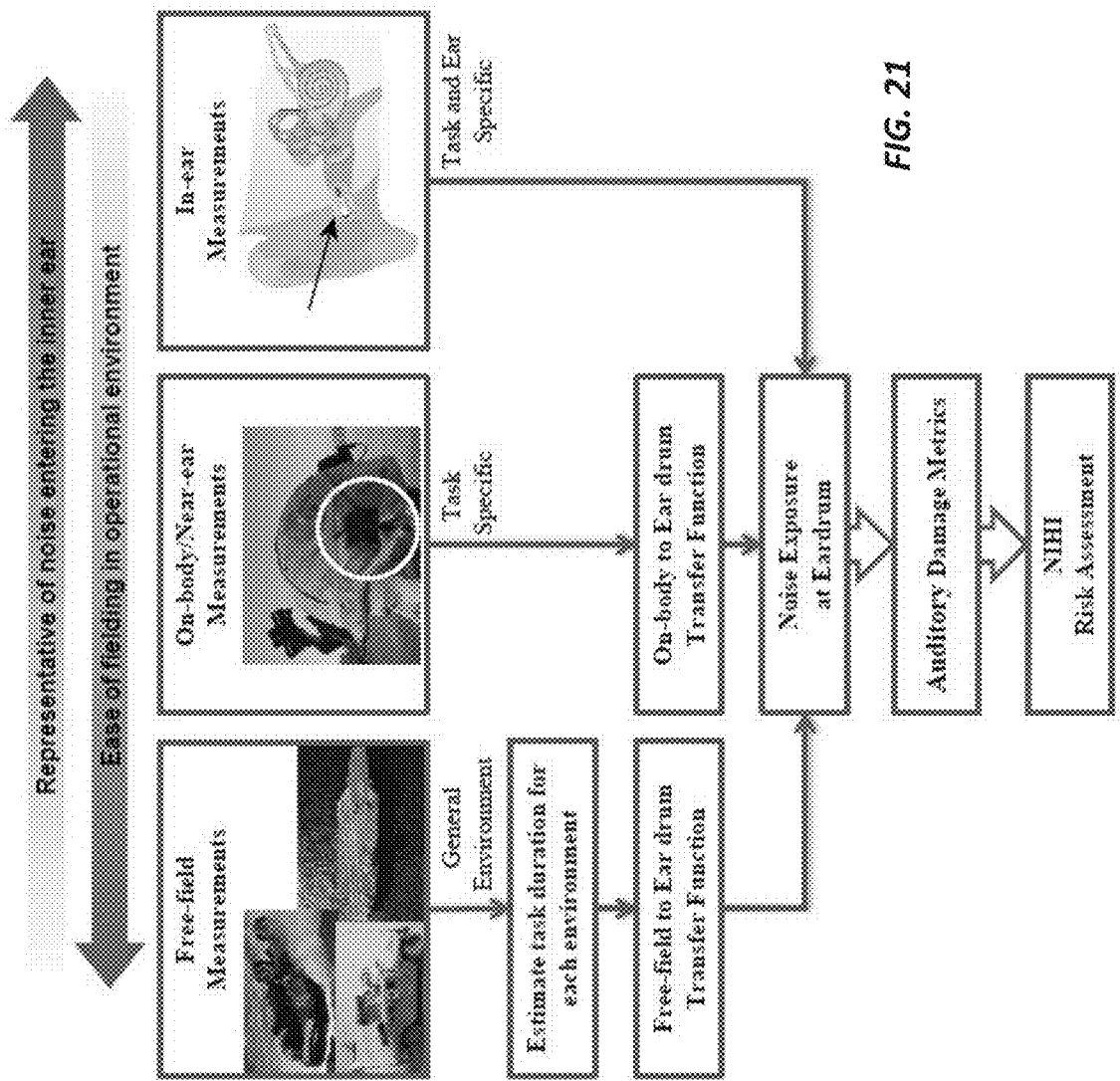
FIG. 21 is a diagram illustrating how dosimeter collection is affected by microphone placement in accordance with some embodiments.

According to some embodiments, in-ear dosimetry eliminates the need for on-body to in-ear transfer function. Furthermore, a microphone positioned in the ear can directly measure noise exposure from headphones as well as noise suppression from HPDs. FIG. 21 is a diagram illustrating how the placement of the microphone for dosimeter measurements affects the process used in assessing risk of NIHL in accordance with some embodiments. The ideal microphone placement for personal dosimetry is in the ear since it requires very few assumptions about the activities of the individual. However, in-ear dosimetry may interfere with standard hearing protection, situational awareness, comfort, and cause occlusion making it not practical for 24 hour dosimetry or long-term use. Near-ear dosimetry can provide a good compromise of fidelity and practical use in fieldings.

Figure 22:
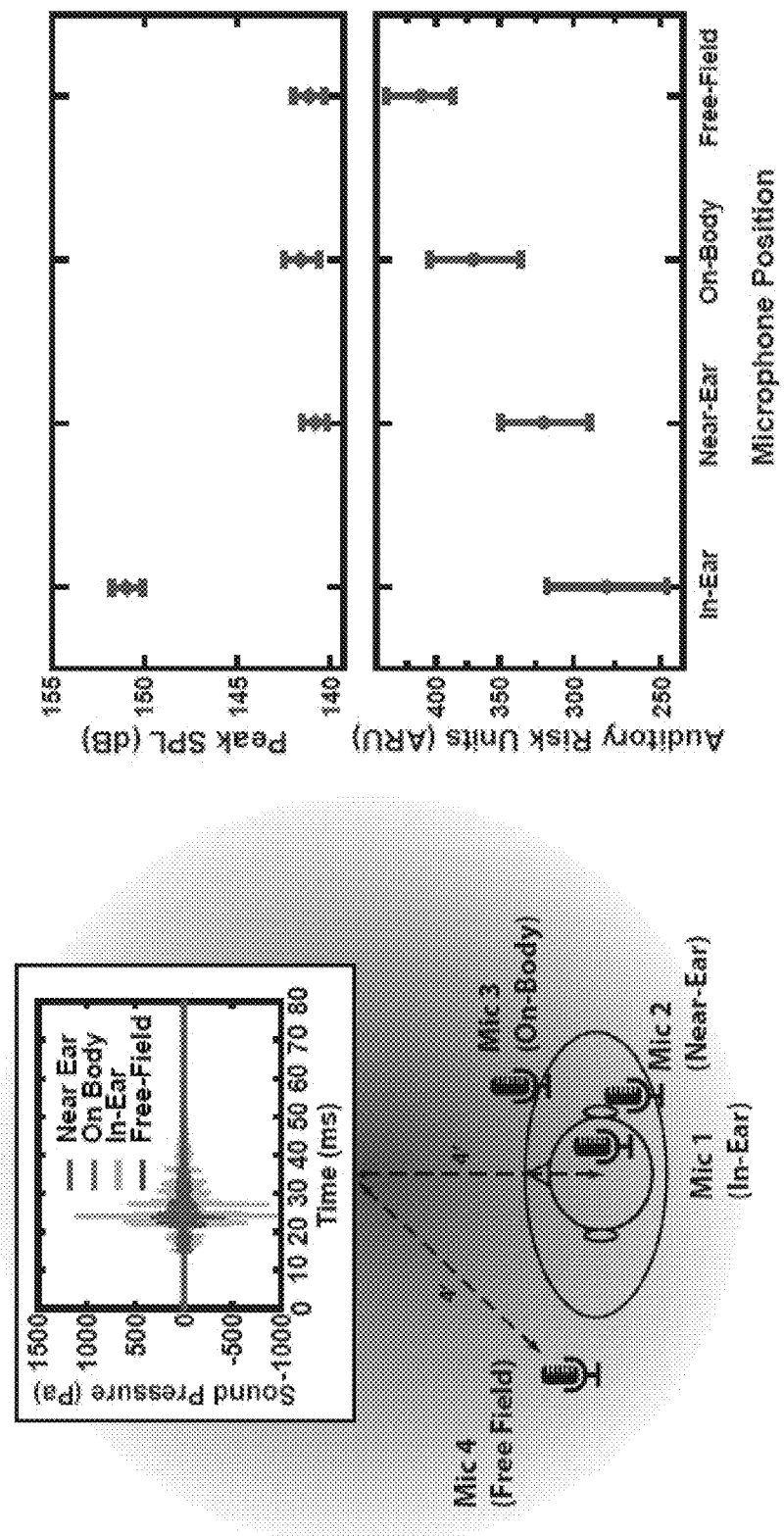
FIG. 22 is a series of plots comparing peak SPL and AHAAH model at four recording locations for impulse noise in accordance with some embodiments.

To illustrate the differences between the various different microphone placements, a laboratory test was performed to record a series of impulses from four microphone positions simultaneously, as shown in FIG. 22, in accordance with some embodiments. FIG. 22 is a series of plots comparing peak SPL (upper right) and AHAAH model (lower right) at 4 recording locations for impulse noise in accordance with some embodiments.

The setup used a GRAS 45CB acoustic test fixture to obtain in-ear measurements; the "near-ear" dosimeter microphone was mounted on the test fixture as shown in FIG. 15. All of the pressure microphones were oriented so that the sound-pressure wave from an impulsive source was at a 90-degree angle of incidence to the diaphragm, so no angle-of-incidence correction is required.

Since all of recordings were made simultaneously for each impulse, the damage risk to the inner ear is intrinsically identical regardless of the measurement location. For a frontal impulse noise source (0-degree azimuth), the free-field, on-body and near-ear microphones all produce similar peak and A-weighted sound-pressure levels, but the in-ear measurement is amplified by nearly 10 dB due to the outer-ear and pinna. Current exposure metrics, such as $L_{Aeq,8h}$, are based on free-field measurements, because they are more convenient to obtain with a sound-level meter. However, an in-ear measurement may be a more accurate predictor of hearing damage than a free-field measurement, even if it is more difficult to measure in practice.

As previously mentioned in Section 2.2, the AHAAH model provides transfer functions, that include various assumptions, to correct for microphone placement. The location options supported by AHAAH are (1) free-field, (2) ear-canal entrance, or (3) eardrum, and were applied appropriately to the data shown in FIG. 22. For a free-field measurement, the AHAAH model assumes that the energy is transmitted directly to the ear (i.e., that the measurement location and the head are in the same place and that the sound source is aligned in azimuth and elevation with the ear canal), providing a worst case estimate of the transmission. Due to this assumption, the reported ARU value was highest for this sample dataset when calculated using free-field-like conditions. If the ARU in-ear value is taken as ground truth, the error in predicted risk increases as the distance of the measurement from the ear increases.

This experiment was conducted for a single source angle (frontal), but relationships between the microphone measurements will depend on the location of the source as well as placement of the on-body microphone. This issue of on-body microphone placement is not accounted for in the current ASA and ANSI Standard 51.25 specification for personal noise dosimeters (ANSI, 1991), and may be even more important when considering impulsive or complex noise environments. Finally, metrics should be adapted for in-ear dosimetry when combined with hearing protection devices. In the most recent version of the AHAAH model, as described in MIL-STD-1474E, a hearing protector simulator is included to better estimate exposure at the ear drum.

The prevalence of NIHL in the military has continued to increase over the past decade, even as Department of Defense efforts to protect and conserve hearing have increased. A key step in developing strategies to reduce NIHL is to improve the ability to measure noise exposure for the individual and to predict the risk of hearing injury accurately. The MIT LL second-generation dosimeter prototype is in development to help bridge the gap between COTS dosimeters that provide persistent on-body noise exposure measurements for industrial environments, and large-SWaP laboratory-grade sound-pressure meters capable of measuring the extreme levels and broadband characteristics that may be encountered in military noise environments.

Translating noise exposure to auditory damage through appropriate metrics is still an open area of research. Progress in this area has been slow due to the very few data sets that contain both noise exposure and audiometric data for humans. Proposed near-term collections with the MIT LL dosimeter prototype include Marine training exercises with live fire and blasts as engineering tests of the system. Future collections also may include coordinated audiometry and potentially other physiological data such as genetic biomarkers. Collections of this type will support the continued validation of proposed damage risk metrics and development of more comprehensive modeling of auditory damage from noise. Finally, it is important to note that a potential future use for personalized dosimetry relates to recent studies that show promising results for reducing NIHL with therapeutic agents. When administered within one hour of the exposure, pharmacological interventions may provide as much as 30 dB of protection against a permanent threshold shift. On-body noise dosimetry may be used to provide an alert to soldiers and medics when a noise exposure exceeds a dangerous threshold. This immediate feedback could improve the chances of delivering therapy to individuals who need it during the short window of opportunity in which it would be most effective.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the analog and/or digital circuitry elements disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the analog and/or digital circuitry disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety, including:

Ahroon et al., "Analysis of Army-wide hearing conservation database for hearing proles related to crew-served and individual weapon systems," *Noise & Health* 13, 76 (2011);

American Institute of Biological Sciences (AIBS), *Peer Review of Impulse Noise Injury Models* (AIBS 2010);

American National Standards Institute (ANSI), *Specification for Sound Level Meters*, S1.4-1983 (R2006) (ANSI 1983);

ANSI, *Specification for Personal Noise Dosimeters*, S1.25-1991 (ASA 98-1991) (ANSI 1991);

Berger et al., *The Noise Manual* (AIHA 2003);

Boroditsky et al., "Predicting shipboard noise using 3-d acoustic modeling," *Noise Control Eng. J.* 55, 246-56 (2007);

Bruel, "Do we measure damaging noise correctly?" *Noise Control Eng. J.* 8, 52-60 (1997);

Cooper et al., "The Department of Defense epidemiologic and economic burden of hearing loss study," *Military Med.* 179, 1458-64 (2014);

Defence Res. & Dev. Canada, Toronto Research Centre, DRDC-RDDC-2015-R243, *A comparison of metrics for impulse noise exposure* (2015);

Goley et al., "Kurtosis-corrected sound pressure level as a noise metric for risk assessment of occupational noises," *J. Acoustical Society of America* 129, 1475-81 (2011);

Hamernik et al., "Interaction of continuous and impulse noise: Audiometric and histological effects," *J. Acoustical Society of America* 55, 117-21 (1974);

Hamernik et al., "The energy spectrum of an impulse: Its relation to hearing loss," *J. Acoustical Society of America* 90, 197-204 (1991);

Helfer et al, "Noise-induced hearing injury and comorbidities among postdeployment US Army soldiers: April 2003-June 2009," *Am. J. Audiology* 20, 33-41 (2011);

Kardous et al., "Evaluation of smartphone sound measurement applications," *J. Acoustical Society of America*, 135, EL186-EL192 (2014);

Kardous et al., "Limitations of using dosimeters in impulse noise environments," *J. Occup. & Envt'l Hygiene* 1, 456-62 (2004);

Kardous et al., "Noise dosimeter for monitoring exposure to impulse noise," *Applied Acoustics* 66, 974-85 (2005);

Knowles Electronics, Inc., *Walk induced head vibrations and hearing aid design* TB5;

Kryter, *The Effects of Noise on Man* (Academic 1985);

Kuhn, "The pressure transformation from a diffuse sound field to the external ear and to the body and head surface," *J. Acoustical Society of America* 65, 991-1000 (1979);

Le Prell et al., "Prevention of Noise-Induced Hearing Loss: Potential Therapeutic Agents," in *Springer Handbook of Auditory Res.*, 40:285-338 (Springer 2012);

McKinley, "LIAeq100 ms, an a-duration adjusted impulsive noise damage risk criterion," *J. Acoustical Society of America* 138:1774;

Nakashima et al., "Hearing, communication and cognition in low-frequency noise from armoured vehicles," *Noise & Health* 9:35 (2007).

Nakashima et al., "Review of weapon noise measurement and damage risk criteria: Considerations for auditory protection and performance," *Military Med.* 180:402-08 (2015);

Price et al., "Insights into hazard from intense impulses from a mathematical model of the ear," *J. Acoustical Society of America* 90:219-27 (1991);

Price, "Impulse noise hazard as a function of level and spectral distribution," in Salvi et al., *Basic and Applied Aspects of Noise-Induced Hearing Loss* (Springer 1986);

Price, "Validation of the Auditory Hazard Assessment Algorithm for the Human with impulse noise data," *J. Acoustical Society of America* 122:2786-2802 (2007);

Qiu et al., "The kurtosis metric as an adjunct to energy in the prediction of trauma from continuous, non-Gaussian noise exposures," *J. Acoustical Society of America* 120: 3901-06 (2006);

Qiu et al., "The value of a kurtosis metric in estimating the hazard to hearing of complex industrial noise exposures," *J. Acoustical Society of America*, 133:2856-66 (2013);

Rovig et al., "Hearing health risk in a population of aircraft carrier flight deck personnel," *Military Med.* 169:429-32 (2004);

Shaw et al., "Transformation of sound-pressure level from the free field to the eardrum presented in numerical form," *J. Acoustical Society of America* 78:1120-23 (1985);

Sheeld et al., "The relationship between hearing acuity and operational performance in dismounted combat," in *Proceedings of the Human Factors and Ergonomics Society Annual Meeting 59:1346-50 (2015);

Sun et al., "Development and validation of a new adaptive weighting for auditory risk assessment of complex noise," Applied Acoustics 103:30-36 (2016);

Theodoroff et al., "Hearing impairment and tinnitus: Prevalence, risk factors, and outcomes in US service members and veterans deployed to the Iraq and Afghanistan wars," Epidem. Rev., 37:71-85 (2015);

U.S. Army Med. Res. & Dev. Command, *Blast overpressure studies with animals and man: Walk-up study* (1993);

U.S. Army Res. Lab., ARL-RP-0521, *Mathematical Model of the Ear's Response to Weapons Impulses* (2015);

U.S. Department of Veterans Affairs, *Annual Benefits Report Fiscal Year 2015* (2015);

U.S. Dept. of Defense, 6055.12, *Hearing Conservation Program* (2010);

U.S. Dept. of Defense, MIL-STD-1474E, *Design Criteria Standard: Noise Limits* (2015);

U.S. Dept. of Health & Human Services, 98-126, *Criteria for a Recommended Standard: Occupational Noise Exposure* (1998).

U.S. Dept. of Health & Human Services, EPHB 309-05h, *An Analysis of the Blast Overpressure Study Data Comparing Three Exposure Criteria* (2009);

U.S. Dept. of Interior, Bureau of Mines, *Response Variations of a Microphone Worn on the Human Body* 7810 (1973);

U.S. Navy, 5100.19E, *Safety and Occupational Health (SOH) Program Manual for Force Afloat* ch. B4 (2007);

U.S. patent application Ser. No. 14/101,802, filed on Dec. 10, 2013, entitled "Methods and Apparatus for Recording Impulsive Sounds;"

Ward et al., "Effective quiet and moderate TTS: Implications for noise exposure standards," *J. Acoustical Society of America,* 59:160-65 (1976);

Yankaskas et al., "Landing on the roof: CVN noise," *Naval Eng. J.,* 111:23-34 (1999); and Zagadou et al., "Impulse noise injury prediction based on the cochlear energy," *Hearing Research* 1-16 (2016).

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A system for continuously collecting sound pressure due to both continuous noise and impulse noise in an environment, the system comprising:

a first sensor to obtain a first analog signal representative of impulse noise sound pressure in a first amplitude range from about 100 dB to about 180 dB;

a second sensor to obtain a second analog signal representative of continuous noise sound pressure in a second amplitude range from about 20 dB to about 140 dB, the second amplitude range being different from the first amplitude range;

at least one analog-to-digital converter (ADC), operably coupled to the first sensor and the second sensor, to sample:

the first analog signal at a first sampling rate equal to or greater than twice the reciprocal of a minimum impulse noise rise time in the first analog signal, thereby generating a first digital signal; and the second analog signal at a second sampling rate equal to or greater than twice the reciprocal of a minimum impulse noise rise time in the second analog signal, thereby generating a second digital signal;

a first accelerometer to obtain a first accelerometry signal representative of accelerometry data in close proximity to the first sensor and the second sensor; and a second accelerometer to obtain at least one second accelerometry signal representative of accelerometry data remote from the at least one first sensor and the at least one second sensor relative to the at least one first accelerometer, at least one processor including:

a first combining node to combine the first digital signal and the second digital signal into a combined audio signal having a combined amplitude range, the combined amplitude range being larger than the first amplitude range, larger than the second amplitude range, and less than or about equal to the sum of the first amplitude range and the second amplitude range, the combined audio signal representing both the continuous noise and the impulse noise in the environment;

a shock-artifact detection filter to identify a time frame potentially including a shock artifact based at least in part on the first accelerometry signal and the second accelerometry signal;

a frequency filter to generate a background-removed audio signal by removing background noise from the combined audio signal;

an adaptive filter to estimate the shock artifact based at least in part on the identified time frame and the background-removed audio signal; and a second combining node to produce a shock-artifact-free audio signal by subtracting the estimated shock artifact from the combined audio signal.

2. The system of claim 1, wherein the system is configured to be worn by a subject.

3. The system of claim 2, wherein:

the first sensor, the second sensor, and the first accelerometer are configured to be worn on the subject's head; and the second accelerometer is configured to be worn on the subject's torso.

4. The system of claim 3, further comprising:

a third sensor to obtain a third analog signal representative of impulse noise sound pressure in the first amplitude range;

a fourth sensor to obtain a fourth analog signal representative of continuous noise sound pressure in the second amplitude range; and a third accelerometer to obtain a third accelerometry signal representative of accelerometry data in close proximity to the third sensor and the fourth sensor, wherein:

the first sensor, the second sensor, and the first accelerometer are configured to be positioned on a first side of the subject's head; and the third sensor, the fourth sensor, and the third accelerometer are configured to be positioned on a second side of the subject's head, the second side opposite the first side.

5. The system of claim 1, wherein the first accelerometer is a triaxial accelerometer.

6. The system of claim 1, wherein the second accelerometer is a nine-channel accelerometer.

7. The system of claim 1, further comprising at least one memory device for storing a representation of the shock-artifact-free audio signal.

8. The system of claim 1, wherein:

the first amplitude range is from about 115 dB to about 180 dB;

the second amplitude range is from about 75 dB to about 140 dB; and the combined amplitude range is less than about 105 dB.

9. A system for continuously collecting sound pressure due to both continuous noise and impulse noise in an environment, the system comprising:

at least one processor, operably coupled to:

a first sensor to obtain a first audio signal representative of impulse noise sound pressure in a first amplitude range from about 100 dB to about 180 dB, sampled at a first sampling rate equal to or greater than twice the reciprocal of a minimum impulse noise rise time in the impulse noise sound pressure;

a second sensor to obtain a second audio signal representative of continuous noise sound pressure in a second amplitude range from about 20 dB to about 140 dB, sampled at a second sampling rate equal to or greater than twice the reciprocal of a minimum impulse noise rise time in the continuous noise sound pressure, the second amplitude range being different from the first amplitude range;

a first accelerometer to obtain a first accelerometry signal representative of accelerometry data, wherein the at least one processor includes:

a first combining node to combine the first audio signal and the second audio signal into a combined audio signal having a combined amplitude range, the combined amplitude range being larger than the first amplitude range, larger than the second amplitude range, and less than or about equal to the sum of the first amplitude range and the second amplitude range, the combined audio signal representing both the continuous noise and the impulse noise in the environment;

a shock-artifact detection filter to identify a time frame potentially including a shock artifact based at least in part on the first accelerometry signal;

a frequency filter to generate a background-removed audio signal by removing background noise from the combined audio signal;

an adaptive filter to estimate the shock artifact based at least in part on the identified time frame and the background-removed audio signal; and a second combining node to produce a shock-artifact-free audio signal by subtracting the estimated shock artifact from the combined audio signal.

10. The system of claim 9, wherein the first accelerometer is a triaxial accelerometer.

11. The system of claim 9, further comprising at least one memory device for storing a representation of the shock-artifact-free audio signal.

12. The system of claim 9, further comprising at least one communication interface for transmitting a representation of the shock-artifact-free audio signal.

13. The system of claim 9, wherein:

the first amplitude range is from about 115 dB to about 180 dB;

the second amplitude range is from about 75 dB to about 140 dB; and the combined amplitude range is less than about 105 dB.

14. A method for continuously collecting sound pressure due to both continuous noise and impulse noise in an environment, the method comprising:

obtaining a first audio signal representative of impulse noise sound pressure in a first amplitude range from about 100 dB to about 180 dB, sampled at a first sampling rate equal to or greater than twice the reciprocal of a minimum impulse noise rise time in the impulse noise sound pressure;

obtaining a second sensor to obtain a second audio signal representative of continuous noise sound pressure in a second amplitude range from about 20 dB to about 140 dB, sampled at a second sampling rate equal to or greater than twice the reciprocal of a minimum impulse noise rise time in the continuous noise sound pressure, the second amplitude range being different from the first amplitude range;

obtaining a first accelerometry signal representative of accelerometry data;

combining the first audio signal and the second audio signal into a combined audio signal having a combined amplitude range, the combined amplitude range being larger than the first amplitude range, larger than the second amplitude range, and less than or about equal to the sum of the first amplitude range and the second amplitude range, the combined audio signal representing both the continuous noise and the impulse noise in the environment;

detecting a time frame potentially including a shock artifact based at least in part on the first accelerometry signal;

generating a background-removed audio signal by removing background noise from the combined audio signal with a frequency filter;

applying an adaptive filter to estimate the shock artifact based at least in part on the identified time frame and the background-removed audio signal; and subtracting the estimated shock artifact from the combined audio signal to produce a shock-artifact-free audio signal.

15. The method of claim 14, wherein:

the first amplitude range is from about 115 dB to about 180 dB;

the second amplitude range is from about 75 dB to about 140 dB; and the combined amplitude range is less than about 105 dB.

* * * * *